(12) United States Patent
Tanaka

(10) Patent No.: US 7,336,012 B2
(45) Date of Patent: Feb. 26, 2008

(54) MOTOR, ROBOT, SUBSTRATE LOADER, AND EXPOSURE APPARATUS

(75) Inventor: Keiichi Tanaka, Tokyo (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 11/030,155

(22) Filed: Jan. 7, 2005

(65) Prior Publication Data

US 2005/0115352 A1   Jun. 2, 2005

Related U.S. Application Data

(63) Continuation of application No. PCT/JP2003/008308, filed on Jun. 30, 2003.

(30) Foreign Application Priority Data

Jul. 10, 2002  (JP) .............................. 2002-200843
Aug. 8, 2002  (JP) .............................. 2002-230916

(51) Int. Cl.
*H02K 17/44* (2006.01)
(52) U.S. Cl. ...................... 310/112; 310/114
(58) Field of Classification Search ................ 310/112, 310/114; 74/490.03
See application file for complete search history.

(56) References Cited

U.S. PATENT DOCUMENTS

| | | | | |
|---|---|---|---|---|
| 4,373,147 A | | 2/1983 | Carlson, Jr. .................. 318/48 |
| 5,105,454 A | * | 4/1992 | Saito et al. .................... 378/71 |
| 6,543,306 B1 | * | 4/2003 | Wakabayashi et al. ... 74/490.03 |
| 6,721,496 B2 | * | 4/2004 | Smith .......................... 388/800 |
| 6,876,144 B2 | * | 4/2005 | Peng ..................... 310/156.26 |
| 6,886,154 B2 | * | 4/2005 | Okuyama ..................... 716/21 |
| 6,893,204 B1 | * | 5/2005 | Suzuki et al. ............ 414/744.5 |
| 2003/0159535 A1 | * | 8/2003 | Grover et al. ........... 74/490.04 |
| 2004/0001750 A1 | * | 1/2004 | Kremerman ............. 414/744.1 |

FOREIGN PATENT DOCUMENTS

| | | |
|---|---|---|
| JP | 63-217968 | 9/1988 |
| JP | 11-162838 | 6/1999 |

* cited by examiner

*Primary Examiner*—Dang Le

(57) ABSTRACT

An apparatus that reduces vibration generation and magnetic leakage, wherein the apparatus is a motor, an articulated serial robot that has a motor built in, a substrate loader that includes the articulated robot, and a related exposure apparatus equipped with the substrate loader. The motor includes a drive shaft to drive the motor; a rotor attached with the shaft; and a stator that opposes the rotor and causes an electromagnetic force to act between the rotor and the stator to drive the drive shaft; an RC stator, for reaction force cancellation attached with the stator; an RC rotor for reaction force cancellation, opposing the RC stator; and a counterweight sleeve attached with the RC rotor, wherein the reaction force, which is applied to the stator via the drive shaft when the counterweight sleeve rotates in a direction opposite that of the drive shaft, is cancelled.

22 Claims, 15 Drawing Sheets

MOTOR, ROBOT, SUBSTRATE LOADER, AND EXPOSURE APPARATUS

CROSS-REFERENCE TO RELATED APPLICATIONS

This is a continuation application, filed under 35 U.S.C. §111(a), of International Application PCT/JP2003/008308 filed on Jun. 30, 2003, the contents of which are incorporated herein by reference.

BACKGROUND OF THE INVENTION

1. Field of the Invention

The present invention relates to a motor that has added improvements to reduce vibration generation and magnetic leakage as well as an articulated serial robot that has a motor built in. In addition, the present invention relates to a substrate loader that includes an articulated serial robot, with added improvements to reduce or restrict vibration and increase high speed handling performance, and/or as well as an exposure apparatus equipped with the substrate loader.

2. Description of the Related Art

FIG. 14 illustrates a formation-related apparatus and control system overview of an entire optical system of an electron beam exposure apparatus of a projection exposure system.

An illumination optical lens barrel 201 is arranged at the upper portion of electron beam exposure apparatus 200. A vacuum pump (not shown in the drawing) is connected to the optical lens barrel 201 and performs vacuum exhaust within the lens barrel.

An electron gun 203 is arranged at the upper portion of the lens barrel 201 (including the mask chamber), and an electron beam is irradiated downward. A condenser lens 204, an electron beam deflector 205 and a mask M are arranged in sequence below the electron gun 203. The electron beam irradiated from the electron gun 203 is converged by the condenser lens 204 as it is sequentially scanned in the horizontal direction in FIG. 4 via the deflector 205, and illumination of the small regions (subfields) of the mask M within the visual field of the optical system is performed. The above-described illumination optical system has a beam formation aperture and a blanking aperture, etc. (not shown in the drawing).

The mask M is secured via an electrostatic suction, etc., to a chuck 210 provided at the upper portion of a mask stage 211. The mask stage 211 is mounted on a mount body 216.

A drive apparatus 212 is connected to the mask stage 211. The drive apparatus 212 is connected to a control apparatus 215 via a driver 214. In addition, a laser interferometer 213 is installed on the mask stage 211. The laser interferometer 213 is connected to the control apparatus 215. Accurate positional information of the mask stage 211 calculated by the laser interferometer 213 is input to the control apparatus 215. A command is then sent from the control apparatus 215 to the driver 214, and the drive apparatus 212 is driven.

A wafer chamber 206 (vacuum chamber) is shown below a mount body 216. A vacuum pump (not shown in the drawing) is connected to the wafer chamber 206, and the vacuum pump evacuates the inside of the chamber.

A projection lens 224, a deflector 225, etc., are arranged in the projection optical system lens barrel (not shown in the drawing) inside the wafer chamber 206. In addition, a wafer stage (precision equipment) 231 is mounted on the lower surface of the wafer chamber 206 that is further below. A chuck 230 is provided at the upper portion of the wafer stage 231, and a wafer W is secured via an electrostatic suction, or the like.

The electron beam that has passed through the mask M is converged via projection lens 224. The electron beam that has been converged by the projection lens 224 is deflected by deflector 225, and the image of the mask M is resolved at the prescribed position on the wafer W. The projection optical system also has various types of aberration compensation lenses, contrast apertures (not shown in the drawing), etc.

A drive apparatus 232 is connected to the wafer stage 231. The drive apparatus 232 is connected to the control apparatus 215 via a driver 234. In addition, a laser interferometer 233 is installed at the wafer stage 231. The laser interferometer 233 is connected to the control apparatus 215. Accurate positional information of the wafer stage 231 calculated by the laser interferometer 233 is input to the control apparatus 215. Based on this, a command is sent from the control apparatus 215 to the driver 234, and the drive apparatus 232 is driven.

FIG. 15 is a plan view showing a wafer conveyance mechanism within a common wafer chamber. In FIG. 15, a wafer stocker 261 in which a plurality of pre-processed wafers is accommodated and a wafer loader 250 are arranged inside the wafer chamber 206. The wafer is conveyed from the wafer stocker 261 onto the wafer stage 231 via the loader 250, mounted on the wafer stage 231 and supplied to an exposure transfer. The loader 250 has an arm rotatably linked.

In the aforementioned loader 250, the wafers are transported one at a time from the wafer stocker 261 to the wafer stage 231 via an end effector provided on the arm. In addition, the wafers are also conveyed one at a time when returning the wafers from the mask stage 231 to the mask stocker 261 after the transfer has ended.

When the substrate loader is operated at a high speed, the positional accuracy and stabilization times of the end effector decreases. This occurs because vibration increases when operating at high speed, since rigidity of the mechanism portion of the substrate loader does not increase. To deal with the foregoing problem, the residual difference between the actual sample position and the target position is obtained, and the end effector is positioned according to the obtained value. The end effector is positioned according to a rotary encoder and microrotation motor, which is the drive source, provided within the joint portion of the arm equipped with that end effector. First, the rotation angle of that arm is detected by the rotary encoder, and the position of the sample on the end effector is obtained from this rotation angle. At this time, a detection cycle of approximately five times the characteristic frequency of the mechanism portion is generally required. Then, a fine adjustment operation amount is calculated from the deviation between the actual sample position and the target position, a command is provided to the microrotation motor, and the detected rotation angle is fed back.

In the foregoing type of exposure apparatus that uses an electron beam, measures are implemented to control the magnetic field fluctuation that is the cause of the deflection of the electron beam and the vibration generation that causes pattern accuracy to drop. For example, an electromagnetic linear motor with superior controllability and for which magnetic shielding has been implemented is used as the drive source of the wafer stage or the mask stage. In addition, the wafer and mask conveyance sequence is being reviewed, and progress is being made so that adverse effects on exposure accuracy can be avoided.

However, even when the aforementioned measures are implemented, when the wafer conveyance operation is performed during exposure, vibration is generated due to the driving of the conveyance robot (loader), a magnetic field is generated from, for example, the motor built into the robot, and pattern accuracy is reduced. That is, when the drive shafts of the arms of the loader are rotated, a reaction force is applied to the stators of the rotors. In addition, an electromagnetic drive system rotation motor is used as the motor that drives the arms of the loader. Although such an electromagnetic rotation type motor is typically compact, lightweight, energy efficient, and able to be controlled, AC magnetic field leakage from the coil generally occurs and/or DC magnetic field leakage from the magnets generally occurs. In addition, the material point shifts and vibration occurs due to arm movements, such as extension, raising, and/or lowering.

In addition, an arm equipped with an end effector positioned at the extreme distal end of the substrate loader vibrates very little due to movement and rotation; therefore it is necessary to standby until the vibration has settled. Accordingly, handoff of the wafer during the standby time is not possible and the throughput of the apparatus decreases.

For at least the foregoing reasons, it was not possible to simultaneously perform the wafer conveyance operation and the exposure operation. Further, in the wafer conveyance operation, the wafers are conveyed one at a time by a loader, which causes a decrease in the throughput of the exposure apparatus.

In this regard, to ensure pattern accuracy and/or improve the throughput, countermeasures are needed that control leakage magnetic fields and/or the generation of vibration from the robot for wafer conveyance so that it is possible to perform the exposure operation and the wafer conveyance operation together or simultaneously.

SUMMARY OF THE INVENTION

According to an aspect of the invention, there is provided a motor including drive shaft to drive the motor, a main rotor attached with the shaft, a main stator that opposes the main rotor and causes an electromagnetic force to act between the main rotor and the stator to drive the drive shaft, a stator, for reaction force cancellation attached with the main stator, a rotor for reaction force cancellation, opposing the stator, and a counterweight sleeve attached with the rotor, wherein the reaction force, which is applied to the main stator via the drive shaft when the counterweight sleeve rotates in a direction opposite that of the drive shaft, is cancelled.

According to another aspect of the invention, the motor may further include another stator for magnetic cancellation, attached with the main stator and another rotor, for magnetic cancellation, opposing the other stator, wherein magnetism, generated by the main rotor and the main stator via the drive shaft when the magnetism is generated by the other stator and the other rotor, is cancelled.

According to another aspect of the invention, the stator for reaction force cancellation additionally performs magnetic cancellation; a rotor for reaction force cancellation, opposing the stator, additionally performs magnetic cancellation, wherein magnetism, generated by the main rotor and the main stator via the drive shaft when the magnetism is generated by the stator and the rotor, is cancelled.

According to another aspect of the invention, there is provided a robot having at least one arm and an electromagnetic rotation type motor that is a drive source for the at least one arm, including a drive shaft to drive the electromagnetic rotation type motor, a main rotor attached with the drive shaft, a main stator opposing the main rotor and causing an electromagnetic force to act between the main rotor and the main stator to drive the drive shaft, a stator for reaction force cancellation, attached with the main stator, a rotor for reaction force cancellation, opposing the stator, a counterweight sleeve attached with the rotor, wherein the reaction force, which is applied to the main stator via the drive shaft by rotating the counterweight sleeve in a direction opposite that of the drive shaft, is cancelled.

According to another aspect of the invention, the robot may further include another stator for magnetic cancellation, attached with the main stator; and another rotor for magnetic cancellation, opposing the other stator, wherein magnetism, generated by the main rotor and the main stator via the drive shaft when magnetism is generated by the other stator and the other rotor, is cancelled.

According to another aspect of the invention, the stator for reaction force cancellation additionally performs magnetic cancellation, and the cancellation rotor for reaction force cancellation additionally performs magnetic cancellation, wherein magnetism, generated by the main rotor and the main stator via the drive shaft when magnetism is generated by the stator and the rotor, is cancelled.

According to another aspect of the invention, there is provided a substrate loader including at least one arm to load a substrate, an extension mechanism provided with the at least one arm to extend the at least one arm, a raising and lowering mechanism provided with the at least one arm to raise and/or lower the at least one arm, an electromagnetic rotation type motor acting as a drive source for the extension mechanism and the raising and lowering mechanism, and a microrotation mechanism provided with the at least one arm to microrotate the at least one arm.

According to another aspect of the invention, the substrate loader may further include an extension mechanism provided with the at least one arm, and a raising and lowering mechanism provided with the at least one arm, wherein the electromagnetic rotation type motor is a drive source of the extension mechanism and the raising and lowering mechanism.

According to another aspect of the invention, the substrate loader further includes an extension mechanism provided with the at least one arm, and a raising and lowering mechanism provided with the at least one arm, wherein the electromagnetic rotation type motor is a drive source of the extension mechanism and the raising and lowering mechanism.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Figure 1:
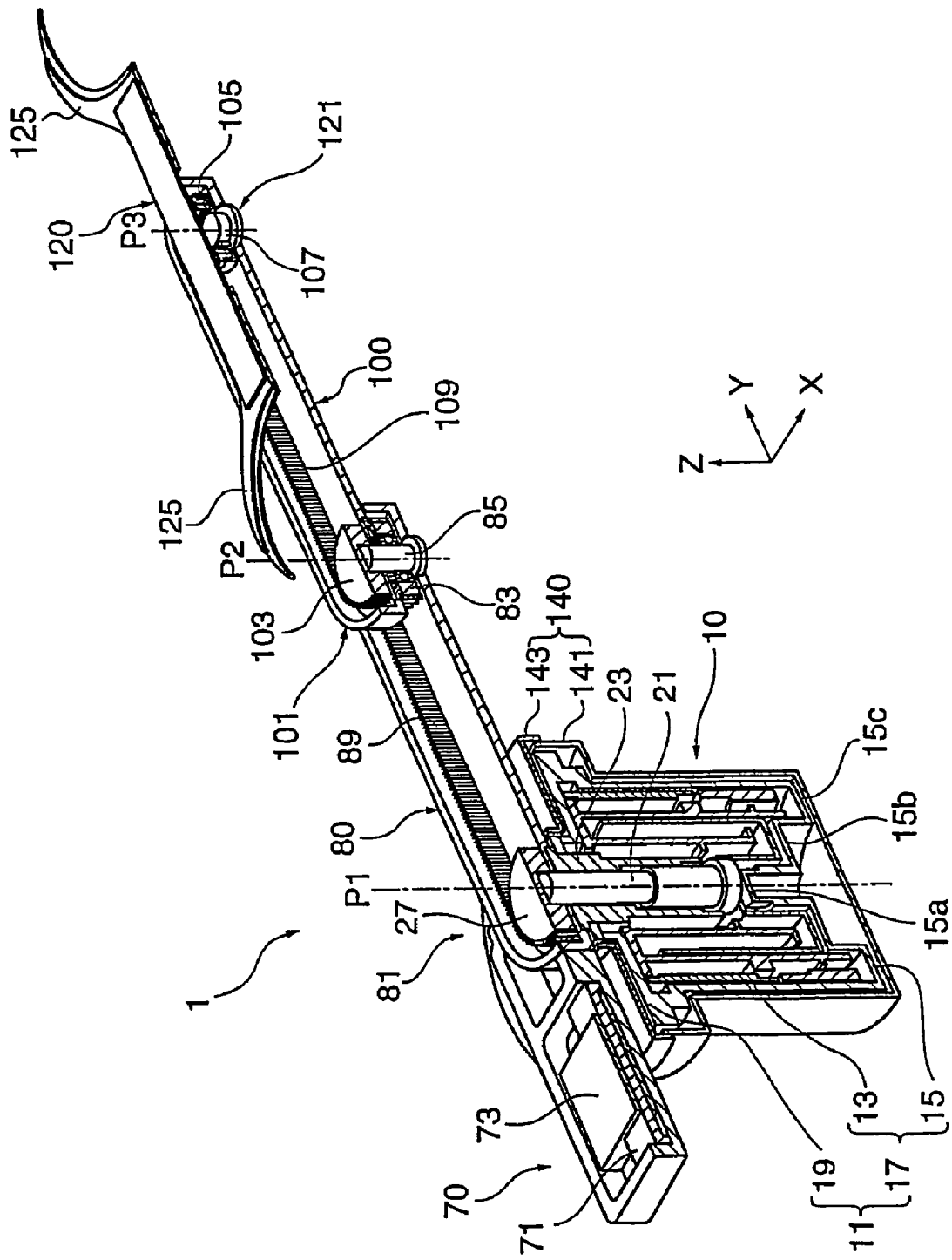
FIG. 1 is a cross-sectional oblique view that shows an overall structure of a substrate loader relating to an aspect of the invention.

Reference will now be made in detail to embodiments of the present invention, examples of which are illustrated in the accompanying drawings, wherein like reference numerals refer to the like elements throughout. The embodiments are described below to explain the present invention by referring to the figures.

According to various aspects of the present invention, the aforementioned problems are taken into account, and there is provided a robot equipped with a motor that restricts vibration generation and magnetic leakage. In particular, one embodiment of the invention relates to a substrate loader that includes a type of robot that is capable of handling an end effector at a high speed and an exposure apparatus equipped with the substrate loader.

According to an embodiment of the invention, the robot includes a first motor equipped with a drive shaft, a main rotor linked with the drive shaft, and a main stator that opposes the main rotor and causes an electromagnetic force to act between the aforementioned main rotor and the aforementioned main stator to rotate and drive the aforementioned drive shaft. The robot may further be equipped with an RC stator for reaction force cancellation linked with the main stator, an RC rotor for reaction force cancellation that opposes the RC stator, and a counterweight sleeve (CW sleeve) linked with the RC rotor to cancel the reaction force applied to the aforementioned main stator in conjunction with the driving of the aforementioned drive shaft by way of rotating the aforementioned CW sleeve in a direction opposite that of the aforementioned drive shaft.

This reaction force is not necessarily a reaction force resulting from the friction resistance applied to the drive shaft or the loads of the wiring, piping, etc. For example, in an embodiment of the invention, the reaction force resulting from these loads is extremely small, and the reaction force resulting from the moment of inertia of the drive shaft is predominant. As such, when an angular acceleration is applied to a rotor in a rotation drive system in which an electromagnetic force is generated between a rotor and a stator to rotate the rotor, torque in the direction opposite the rotation direction of the rotating body is applied to the stator. Thus, what is generally referred to as a reaction force is the torque in the opposite direction produced in the stator according to the moment of inertia of the drive shaft.

The CW sleeve is rotated in a direction opposite that of the drive shaft to cancel the rotation opposing torque applied to the motor stator, so the rotation reaction force is not transmitted outside the motor and vibration attributable to motor driving is reduced.

A second motor, for example, according to the embodiments of the invention, is a motor equipped with a drive shaft, a main rotor linked with the drive shaft, and a main stator that opposes the main rotor and causes an electromagnetic force to act between the main rotor and the main stator to rotate and drive the drive shaft. The second motor may be further equipped with an MC stator for magnetic cancellation linked with the main stator and an MC rotor for magnetic cancellation that opposes the MC stator and cancels the magnetism generated by the main rotor and the main stator in conjunction with the driving of the drive shaft by way of the magnetism generated by the MC stator and the MC rotor.

For example, because the AC magnetic field that leaks from the main stator and the main rotor is cancelled by the MC stator and the MC rotor, it is possible to reduce leakage of the magnetic field to outside the motor.

A third motor, for example, according to the embodiments of the invention, is a motor equipped with a drive shaft, a main rotor linked with the drive shaft, and a main stator that opposes the main rotor and causes an electromagnetic force to act between the main rotor and the main stator to rotate and drive the drive shaft. The third motor may further be equipped with a cancellation stator for reaction force cancellation and magnetic cancellation linked with the aforementioned main stator, a cancellation rotor for reaction force cancellation and magnetic cancellation that opposes the cancellation stator, and a counterweight sleeve (CW sleeve) that is linked with the cancellation rotor and cancels the reaction force applied to the main stator in conjunction with the driving of the aforementioned drive shaft via rotation of the CW sleeve in a direction opposite that of the aforementioned drive shaft while canceling the magnetism generated by the aforementioned main rotor and main stator in conjunction with the driving of the aforementioned drive shaft via the magnetism generated by the cancellation stator and the cancellation rotor.

For example, a motor may be provided that cancels the rotation reaction force (torque) generated by the motor and the AC leakage magnetic field and in which vibration and magnetic fields have little influence on the exterior.

According to an embodiment of the invention, when a magnetic shield that is made of a material with a high magnetic induction ratio that covers the area of the aforementioned electromagnetic rotation motor while leaving a predetermined space is provided, it is possible to shield the DC magnetic field that leaks from the motor stator (permanent magnet).

According to an embodiment of the invention, a first robot is a robot having a plurality of arms and joints and an electromagnetic rotation type motor is the drive source in which the arms are concentrated. For example, the motor is equipped with at least a drive shaft, a main rotor linked with the shaft, and a main stator that opposes the main rotor and causes an electromagnetic force to act between the main rotor and the main stator to rotate and drive the drive shaft. The motor may be further equipped with an RC stator for reaction force cancellation linked with the main stator, an RC rotor for reaction force cancellation that opposes the RC stator, and a counterweight sleeve (CW sleeve) linked with the RC rotor and cancels that reaction force applied to the main stator in conjunction with the driving of the drive shaft via the rotation of the CW sleeve in a direction opposite that of the drive shaft.

For example, since very little vibration is generated in the aforementioned embodiment of the robot, the aforementioned main motor may be applied to robots used under conditions in which vibration is not desirable.

According to another embodiment of the invention, there is provided a robot having a plurality of arms and joints and an electromagnetic rotation type motor is the drive source in which the arms are concentrated. For example, the motor is equipped with at least a drive shaft, a main rotor linked with the shaft, and a main stator that opposes the main rotor and causes an electromagnetic force to act between the main rotor and the main stator to rotate and drive the aforementioned drive shaft. The motor may be further equipped with an MC stator for magnetic cancellation linked with the main stator and an MC rotor for magnetic cancellation that opposes said MC stator and cancels the magnetism generated by the main rotor and main stator in conjunction with the driving of the drive shaft via the magnetism generated by the MC stator and the MC rotor.

For example, since there is little magnetic field leakage, the aforementioned motor may be applied to robots used under conditions where magnetic field fluctuations are not desirable.

According to another embodiment of the invention, there is provided another type of robot having a plurality of arms and joints and an electromagnetic rotation type motor is the drive source in which the arms are concentrated. For example, the electromagnetic rotation type motor may be equipped with a drive shaft, a main rotor linked with the drive shaft, and a main stator that opposes the main rotor and causes an electromagnetic force to act between the main rotor and the main stator to rotate and drive the drive shaft. The electromagnetic rotation type motor may be further equipped with a cancellation stator for reaction force cancellation and magnetic cancellation linked with the main stator, a cancellation rotor for reaction force cancellation and magnetic cancellation that opposes the cancellation stator, and a counterweight sleeve (CW sleeve) that is linked with the cancellation rotor and cancels the reaction force applied to the main stator in conjunction with the driving of the drive shaft due to the rotation of the CW sleeve in a direction opposite that of the drive shaft while canceling the magnetism generated by the main rotor and main stator in conjunction with the driving of the drive via the magnetism generated by the cancellation stator and the cancellation rotor.

For example, a robot may be provided with little vibration generation and magnetic field leakage and used under operating conditions where vibration and magnetic field fluctuations are not desirable.

According to another embodiment of the invention, there is provided a first arm directly driven by way of a first drive shaft of the aforementioned motor and a second arm driven via a drive belt via a second drive shaft of the aforementioned motor; thereby making it possible to cancel the reaction forces of both the main stator for the aforementioned first drive shaft and the main stator for the aforementioned second drive shaft.

For example, the above-described embodiment may be applied to an articulated serial robot.

According to another embodiment of the present invention, there is provided a mechanism for raising and lowering the aforementioned first arm. For example, the mechanism includes a main mover linked to the aforementioned first arm, a main stator that opposes the main mover, an RC stator for reaction force cancellation that this linked with the aforementioned main stator, an RC mover for reaction force cancellation that opposes the RC stator, and a counterweight (CW) linked to the RC mover. Thus it is possible to cancel the reaction force applied to the aforementioned main stator in conjunction with the raising and lowering of the aforementioned first arm by moving the aforementioned CW in a direction opposite that of the aforementioned first arm.

For example, the above-described embodiment may be applied to an articulated robot additionally movable in the Z direction.

According to another embodiment of the invention, when a magnetic shield made of a material having a high magnetic induction ratio that covers the area of the aforementioned electromagnetic rotation motor while leaving a predetermined space, it is possible to shield leakage of the DC magnetic field emitted from the magnets of the motors.

According to another embodiment of the invention, a substrate loader is a substrate loader equipped with at least a substrate loading arm, which is an extension mechanism of said arm, a raising and lowering mechanism of the arm, and an electromagnetic rotation type motor is the drive source in which the two mechanisms are concentrated. For example, the motor may be any one of the above-described type of motors.

In light of the foregoing, it is possible to provide a substrate loader with little vibration generation and magnetic field leakage.

For example, the raising and lowering mechanism of the aforementioned arm may be equipped with a main mover linked to the arm, a main stator that opposes the main mover, an RC stator for reaction force cancellation that this linked with the aforementioned main stator, an RC mover for reaction force cancellation that opposes said RC stator, and a counterweight (CW) linked to the RC mover. Therefore, it is possible to cancel the reaction force applied to the aforementioned main stator in conjunction with the raising and lowering of the aforementioned arm by moving the aforementioned CW in a direction opposite that of the aforementioned arm.

According to another embodiment of the invention, another type of substrate loader is provided. For example, the substrate loader is a substrate loader equipped with at least a substrate loading arm, the extension mechanism of the arm, the raising and lowering mechanism of the arm, and an electromagnetic rotation type motor is the drive source in which the two mechanisms are concentrated. The substrate loader may further be provided with a microrotation.

For example, a microrotation mechanism may be provided on the substrate loading arm (end effector) to cancel the residual vibration generated by the rotation of this substrate loading arm. As such, it is no longer necessary to stand by until the small vibrations of this arm have settled, and apparatus throughput is improved.

According to an embodiment of the invention, when the aforementioned microrotation mechanism has an actuator that does not generate the disturbing magnetic field of an ultrasonic motor, an air motor, or the like, there is no magnetism leakage from the mechanism and there is no effect on exposure accuracy.

For example, the exposure apparatus may be equipped with a sensitive substrate conveyance system and an optical system that selectively irradiates an energy beam onto the sensitive substrate to form a device pattern on the sensitive substrate. The aforementioned sensitive substrate conveyance system includes any one of the above-mentioned substrate loaders.

Thus, because there is a substrate loader that has no vibration generation or magnetism leakage, the exposure operation may be performed during a substrate conveyance operation that uses this substrate loader and makes it is possible to provide an exposure apparatus that has high throughput while maintaining exposure accuracy. Note that there are no particular limitations on the energy beam for exposure, and it is possible to use ultraviolet light, an x-ray, an electron beam, an ion beam, etc. In addition, the exposure system is also not limited, and embodiments of the present invention can be applied to reduction projection, proximity projection lithography, direct writing, etc. Further explanation of the foregoing will be given below while referring to the drawings.

FIG. 1 is a cross-sectional oblique view that shows an overall structure of a substrate loader relating to an embodiment of the invention.

As shown in FIG. 1, a substrate loader 1 is equipped with a motor unit 10 arranged within a casing 11, a first arm 80 linked with the motor unit 10 by a first joint 81, a second arm 100 linked with the first arm 80 by a second joint 101, and a third arm 120 linked with the second arm 100 by a third joint 121. An end effector 125 is provided at both ends of the third arm 120. A semiconductor wafer is loaded and conveyed onto the end effector 125.

As shown in FIG. 1, the casing 11 includes at least a main unit portion 17, which includes a cylindrical side wall 13 and a bottom wall 15, and ceiling portion 19. The bottom wall 15 of the main unit portion 17 includes a concentric center portion 15a, an intermediate portion 15b around the center portion, and an outermost portion 15c around the intermediate portion 15b. For example, the main and portion may be step-shaped, such that the center portion 15a is the highest portion, and the outermost portion 15c is the lowest portion.

The configuration of the arms is explained herein below.

For example, the first arm 80 is driven via a hollow first arm drive shaft 23 in the vicinity of the center of the motor unit 10. The second arm 100 is driven via a second arm drive shaft (e.g., belt pulley drive shaft) 21 in approximately the center of the motor unit 10. Both shafts 23, 21 are driven according to their respective motor mechanisms within the motor unit 10, and each of the shafts 23, 21 independently rotate around axis P1 (details discussed below). The third arm 120 is driven to rotate in an opposite direction by approximately the same angle as the second arm 100 via the second arm drive shaft 21, which is discussed above. In addition, the third arm 120 may be microdriven by a separate motor 110 of this arm proximal end (details discussed below).

Figure 2:
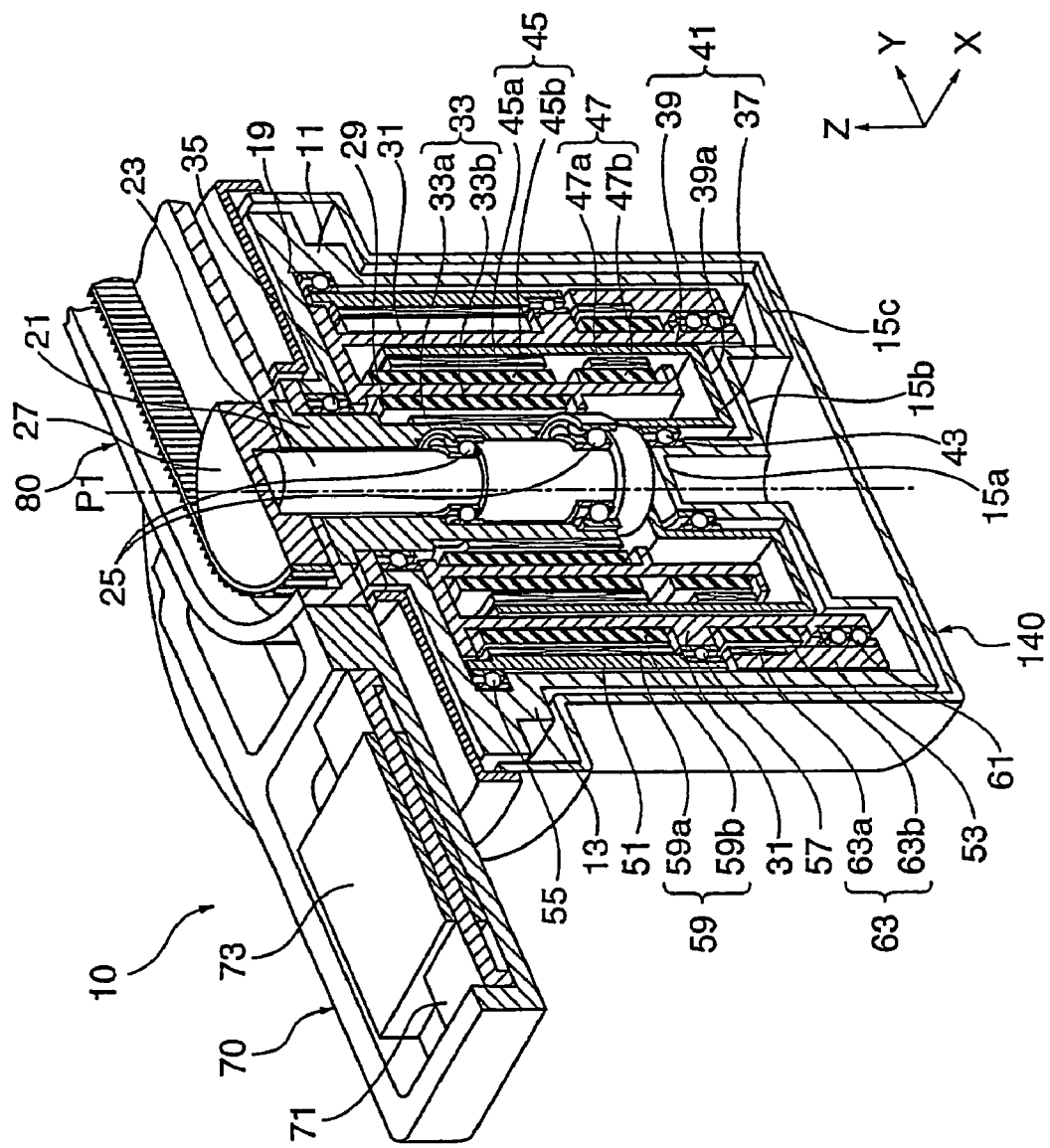
FIG. 2 is a cross-sectional oblique view that shows an enlargement of the structure of a motor unit of the substrate loader of FIG. 1.
Figure 3:
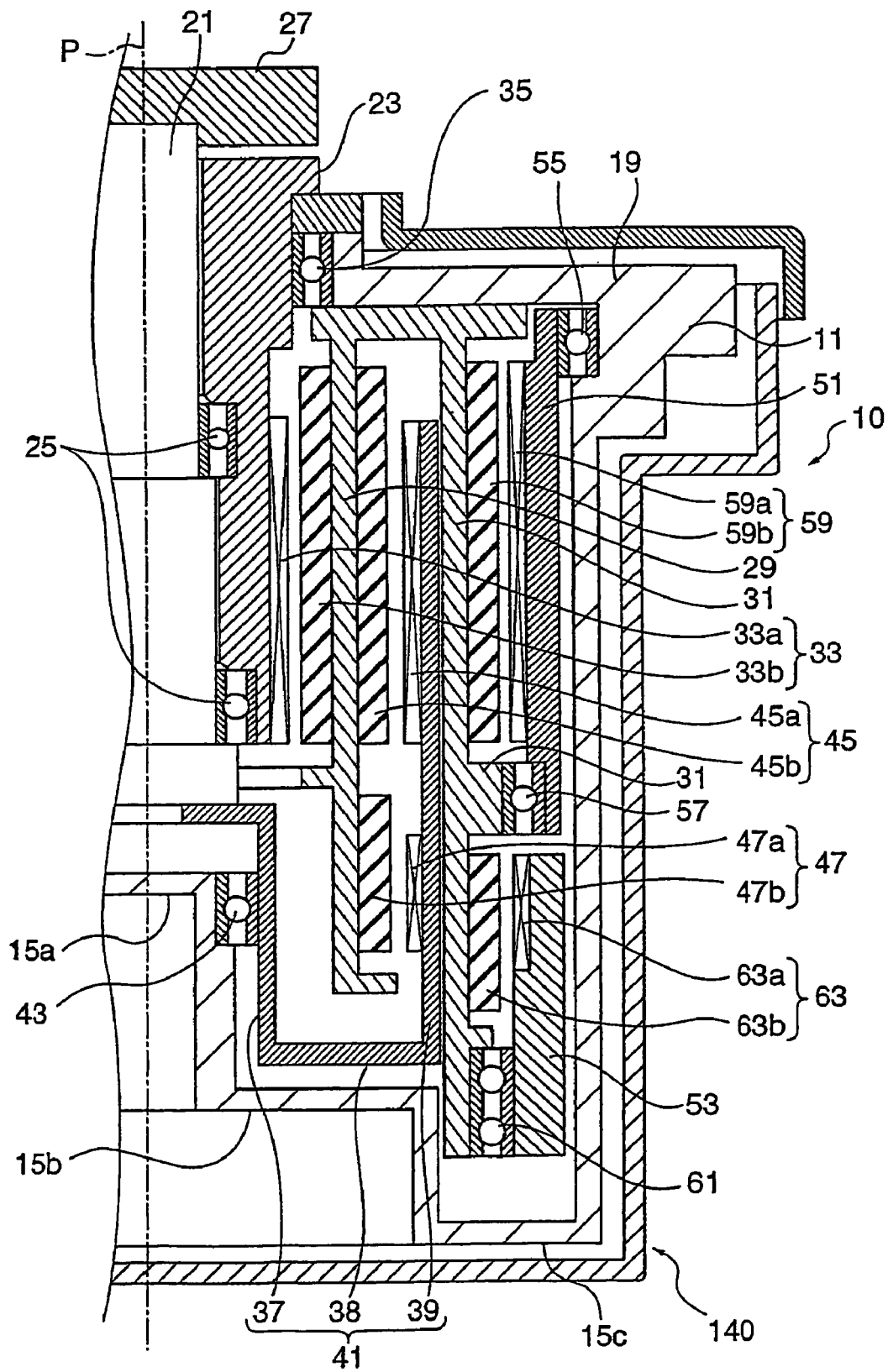
FIG. 3 is a front cross-sectional view of the status in which the motor unit of FIG. 2 has been divided in half vertically.

As shown in FIG. 2 and FIG. 3, provided on the motor unit 10 are a second arm drive shaft 21 that rotates centering on the approximately same axis P1 and a concentric first arm drive shaft 23. For example, arm drive shaft 21 may be a solid cylindrical shape, and the first arm drive shaft 23 may be a substantially cylindrical shape and is arranged to be concentric with the second first arm drive shaft 21 so that it fits the outer circumference of the second arm drive shaft 21.

A bearing 35 may be provided between the first arm drive shaft 23 and the ceiling portion 19 of the casing.

Figure 4:
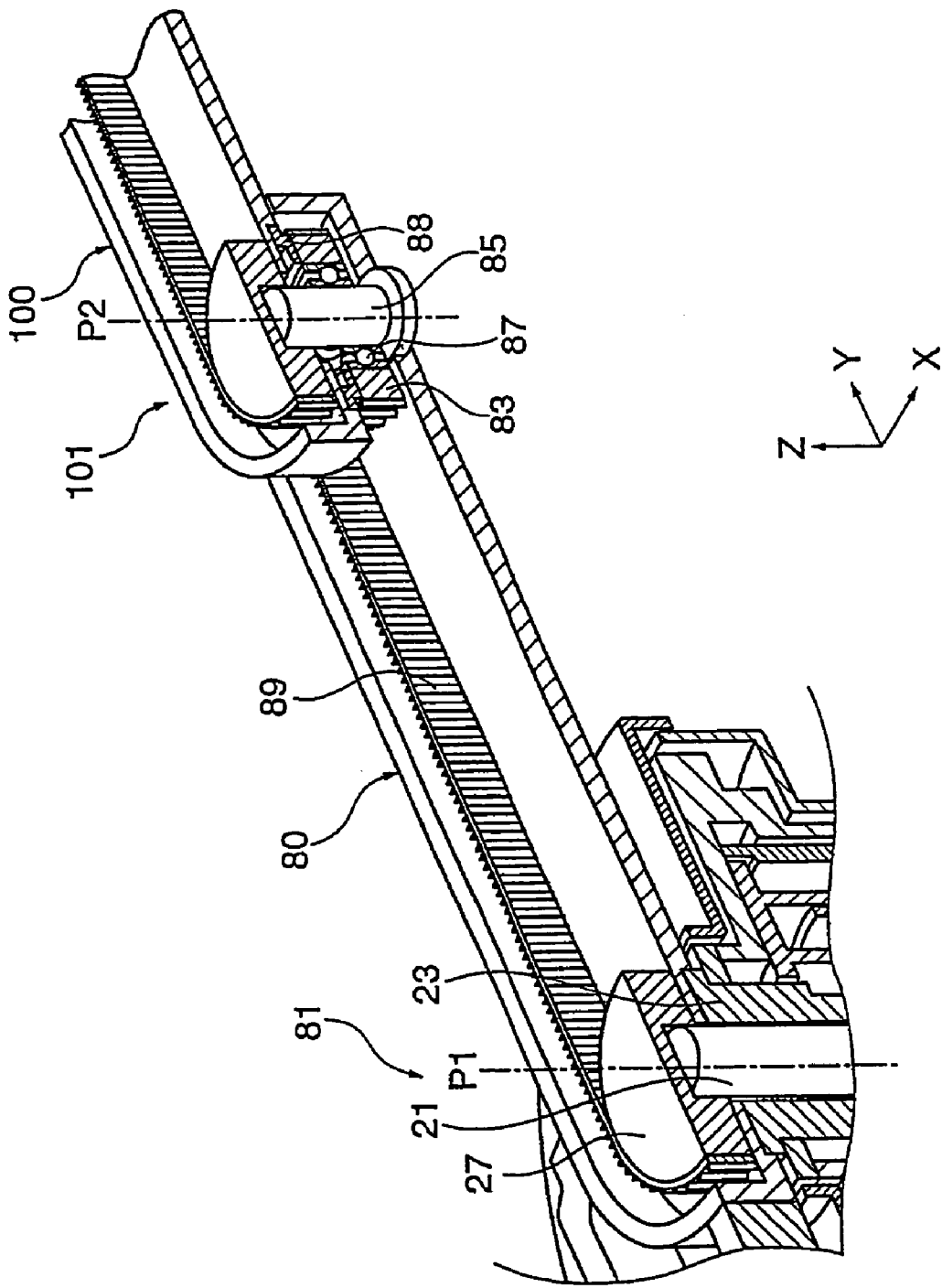
FIG. 4 is a cross-sectional oblique view that shows an enlargement of the structure of a first arm of the substrate loader of FIG. 1.

A peripheral structure of the first arm 80 is explained herein below, according to an embodiment of the invention shown in FIG. 4, wherein the proximal end of the first arm 80 is secured to the first arm drive shaft 23. When the first arm drive shaft 23 is rotated, the first arm 80 is rotated around the center axis P1 (first joint 81) of the first arm drive shaft 23. In addition, the peripheral structure of the first arm 80 may also include a belt drive pulley 27 secured to the second arm drive shaft 21 to be arranged at the proximal end within the first arm 80, and a pulley 83 is arranged at the distal end within this arm 80. For example, the first arm distal end pulley 83 may be rotatably attached with a shaft 85 secured with the distal end of the first arm 80 via a bearing 87 or the like. The belt 89 is provided between both pulleys, e.g., wound.

The rotation of the belt drive pulley 27 in approximately the center of the motor is transmitted to the first arm distal end pulley 83 via a belt 89. The pulley 83 rotates centering on proximal end axis P2 of the second arm 100. A second arm drive shaft 88 is secured with the first arm distal end pulley 83. The second are drive shaft 88 rotates around the axis P2 along with the first arm distal and pulley 83.

For example, the proximal end of the second arm 100 may be secured with the second arm drive shaft 88. Thus, when the second arm drive shaft 88 rotates, the second arm 100 rotates centering about the proximal end axis P2 (second joint 101). As such, by rotating the second arm drive shaft 21 within the motor, the second arm 100 rotates around the distal end axis P2 of the first arm 80.

The structure of the second arm 100 and the third arm 120 is explained herein below according to an embodiment of the invention shown in FIG. 5.

Figure 5:
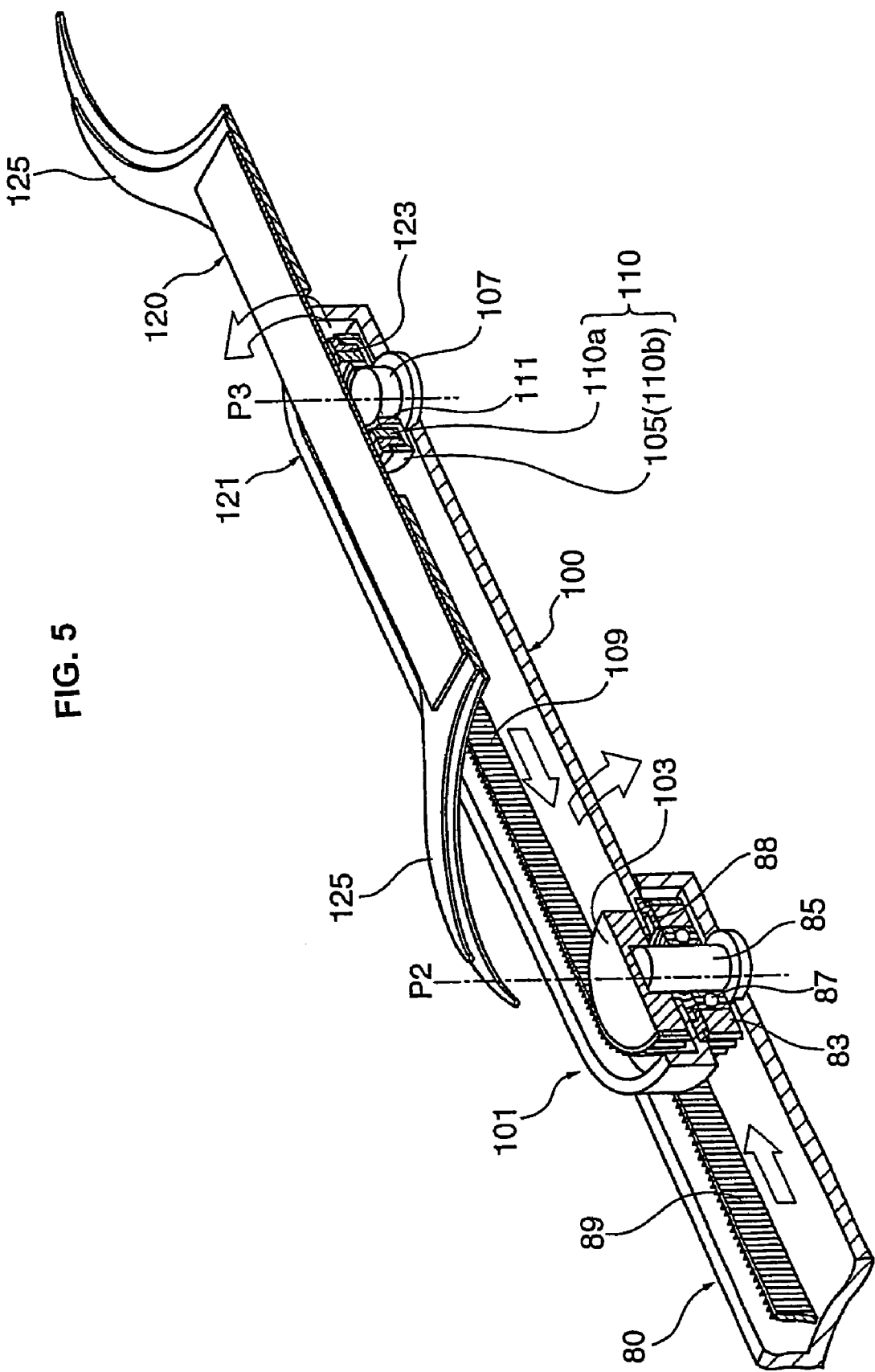
FIG. 5 is a cross-sectional oblique view that shows an enlargement of the structure of a second arm and a third arm of the substrate loader of FIG. 1.

In FIG. 5, a pulley 103 provided with the first arm proximal end shaft 85 is arranged at the proximal end with the second arm 100, and another pulley 105 is arranged at the distal end with the second arm 100. For example, the second arm distal end pulley 105 is rotatably attached to the shaft 107 provided with the distal end of the second arm 100 via the bearing 111. In addition, a belt 109 is provided between the two pulleys, e.g., wound.

For example, the second arm proximal end pulley 103 is secured or provided with the first arm distal end shaft 85. Thus, when the second arm 100 rotates with respect to the first arm 80, this rotation is transmitted to the second arm distal end pulley 105 via belt 109. The rotation may be transmitted according to the second arm proximal end pulley 103 rotating in the opposite direction as the first arm distal end shaft 85.

For example, as shown in FIG. 5, when a belt 89 moves in the direction of the arrow in the figure, the first arm distal end pulley 83 rotates clockwise, and the second arm 100 rotates in the direction of the arrow in the figure (clockwise). However, the second arm proximal end pulley 103 does not rotate, since it is secured to the first arm 80. Therefore, when the belt 109 moves in the direction of the arrow shown in FIG. 5, the second arm distal end pulley 105 rotates counterclockwise, and the third arm 120 rotates in the direction of the arrow in the figure (counterclockwise). For example, the third arm 120 rotates in a direction opposite that of the second arm 100. Ultimately, the third arm 120 rotates only by the same angle in a direction that is the reverse of the rotation direction of the second arm 100, so the relative angle with respect to the motor unit 10 of the third arm 120 will not change.

According to another embodiment of the invention, a rotary encoder (not shown in the figure) may be built into the second arm distal end shaft 107. The rotary encoder detects the rotation angle of the third arm 120 at the third joint 121 and calculates a position of the sample on the end effector 125 from the detected rotation angle. The fine adjustment operation amount is calculated from the deviation between the actual sample position and the target position.

According to another embodiment of the invention, a microrotation motor 110 may be attached with the second arm distal end shaft 107. The microrotation motor 110 microrotates the third arm 120 around the second arm distal end axis P3. For example, microrotation motor 110 uses an air motor or an ultrasonic motor that does not include or require coils or magnets. The rotation motor 110 includes at least a rotor 110a and a stator 110b. The stator 110b may additionally act as the second arm distal end pulley 105. The stator 110b may also have a groove formed along the circumference on the upper surface. In addition, a ring-shaped rotor 110a may be provided in the same groove. The rotor 110a is secured to the third arm drive shaft 123 provided at the center of the third arm. Thus, when the rotor 110a rotates, the third arm 120 rotates by a small degree centering on the center axis P3 (third joint 121). The calculated fine adjustment operation amount discussed above is transmitted to the rotation motor 110 to position the third arm 120 at the target position.

In addition, a cancellation stator and rotor may be provided to cancel the reaction force generated in conjunction with the rotation of this motor 110.

The operation of the at least three arms is explained herein below with reference to an embodiment of the invention shown in FIG. 7. The first arm 80 rotates around the first joint 81 due to the driving of the first arm drive shaft 23. The second arm 100 rotates with respect to the first arm 80 around the second joint 101 due to the driving of the second arm drive shaft 21. In addition, at the third joint 121, the second arm 100 and the third arm 120 rotate in opposite directions at approximately the same angle, so the angle of the third arm 120 with respect to the first arm 80 does not change.

For example, according to the foregoing configuration, when the first arm drive shaft 23 of the motor unit 10 rotates, the first arm 80, the second arm 100 and the third arm 120 rotate relative to each other around the Z axis within the XY plane centering on the first joint 81. In addition, when the second arm drive shaft 21 of that motor unit 10 rotates, the second arm 100 rotates around the Z axis within the XY plane centering on the second joint 101. At this time, the third arm 120 rotates in a direction opposite the rotation direction of the second arm 100. In addition, the first arm drive shaft 23 and the second arm drive shaft 21 are equipped with mechanisms for movement in the Z direction (details discussed below). Therefore, the end effector 125 is able to move or rotate in the XYZ direction, and the mask and the wafer are able to move to a position separate from the prescribed or predetermined position.

The structure of the motor unit is explained herein below with reference to an embodiment of the invention shown in FIG. 3. The second arm drive shaft 21, which extends in the Z direction, and the first arm drive shaft 23, which fits into the circumference of the second arm drive shaft 21, are arranged in approximately the center portion inside of the casing 11. Both drive shafts rotate mutually independently centering on the center axis P1 of the motor unit. Further, the first arm drive shaft 23 may have a substantially cylindrical shape and may be concentrically arranged with the second arm drive shaft 21 at the circumference of the second arm drive shaft 21.

The second arm drive shaft 21 and the first arm drive shaft 23 are provided together or fit via two upper and lower bearings 25. The second arm drive shaft 21 is positioned in approximately the center of the motor unit such that the top portion of the second arm drive shaft 21 has a smaller diameter than a bottom portion. For example, the second arm drive shaft 21 may be designed such that, from the top-down of the shaft 21, there is a small diameter portion, a medium diameter portion, and a large diameter portion. The upper bearing 25 may be arranged at the level between the small diameter portion and the medium diameter portion, and the lower bearing 25 may be arranged at the level between the medium diameter portion and the large diameter portion. The first arm drive shaft 23 and the second arm shaft 21 are independently rotatable. Further, both shafts 21, 23 may be vertically driven via a vertical (Z axis) drive motor 47, which is discussed below. However as shown in FIG. 2 and discussed above, a belt drive pulley 27 may be secured with the upper end of the second arm drive shaft 21, and the upper end portion of the first arm drive shaft 23 may be secured with the first arm 80.

Further, a concentric cylindrical inner core 29 and outer core 31 may be arranged inside a casing 11. Both cores 29 and 31 may be suspended concentrically with the center axis P1 of the motor unit to partition or separate the inside of the casing 11. For example, the upper ends of both cores 29 and 31 are secured to the ceiling portion 19 of the casing 11. The lower end of the inner core 29 extends onto the intermediate portion 15b of the lower wall of the casing, and the lower end of the outer core 31 extends onto the outermost portion 15c of the lower wall of the casing.

The first arm drive shaft rotation motor 33 may be arranged in an inner circumference portion of the inner core 29. For example, the first arm drive shaft rotation motor 33 is an electromagnetic rotation motor that includes at least a coil (main rotor) 33a and a magnet (main stator) 33b. The coil 33a is provided or secured along the outer surface of the lower portion of the first arm drive shaft 23. The magnet 33b is provided or secured so that it opposes the coil 33a along the inner surface of the inner core 29.

According to another embodiment of the invention, an extension member 41 may be secured to a lower end position of the second arm drive shaft 21 at approximately the center of the motor unit. The extension member 41 includes an inside cylinder portion 37 secured to, or provided with, the lower end of the second arm drive shaft 21, a disc portion 38 connected with the lower end of that cylinder portion 37, and an outside cylinder portion 39 connected with the outer circumference of that portion 38. For example, both cylinder portions 37, 39 are arranged concentrically with respect to axis P1.

The inside cylinder portion 37 is positioned to encompass the center portion 15a of the bottom wall of the casing 11, and a bearing 43 is interposed between the bottom wall of the casing 11 and the center portion 15a of the casting 11.

The connection disc portion 38 is positioned at or near the intermediate portion 15b of the lower wall of the casing 11. The outside cylinder portion 39 extends the gap between the inner core 29 and the outer core 31 upward and substantially parallel with both cores 29 and 31. For example, a certain gap is opened between the upper end of the outside cylinder portion 39 and the upper ends (ceiling portion 19 of the casing) of the cores 29, 31 and between cylinder portion 38 and the lower end of the inner core 29.

According to an embodiment of the invention, second arm drive shaft rotation motor 45 is provided at or near the upper portion of the inner circumference of the outside cylinder portion 39 of the extension member 41. For example, the second arm drive shaft rotation motor 45 is an electromagnetic rotation motor that includes at least a coil (main rotor) 45a and a magnet (main stator) 45b. The coil 45a is provided or secured along the inner circumference of an upper portion of the outside cylinder portion 39 of the extension member. The magnet 45b may be secured so that it opposes the coil 45a along the outer circumference surface of the upper portion of the inner core 29. A second arm drive shaft rotation motor 45 may be provided or arranged at a position at the same height as the first arm drive shaft rotation motor 33. Therefore, for example, the second arm drive shaft 21 rotates and is driven along with the extension member 41 via the second arm drive shaft rotation motor 45.

In addition, a linear motor (raising and lowering mechanism) 47 for Z direction movement may be provided at the lower portion of the inner circumference of the extension member 41. A voice coil motor may be used as the linear motor 47. For example, the voice coil motor includes at least a coil (main mover) 47a and a magnet (main stator) 47b. The coil 47a is provided or secured along the inner circumference of the lower portion of the outside cylinder portion 39 of the extension member. The magnet 47b is provided or secured such that it opposes the coil 47a along the outer surface of the lower portion of the inner core 29. The second arm drive shaft 21 and the first arm drive shaft 23 may be vertically driven in the Z axis direction along with the extension member 41 via the linear motor 47.

Thus, according to the aforementioned embodiment of the invention, rotation about the Z axis of the first arm drive shaft 23, rotation around the Z axis of the second arm drive shaft 21, and/or ascending and descending of the first arm drive shaft 23 and/or the second arm drive shaft 21 in the Z direction is performed.

The motor unit 10 may be further equipped with a mechanism that cancels the reaction force and the magnetism that are generated in conjunction with the driving of the arm drive shaft and the belt drive shaft.

Specifically, when the drive shafts 21 and 23 are rotated, a reaction force is applied to the stators of their respective motors. According to this embodiment of the invention, the reaction force refers to both the torque reaction force of the rotation direction and the reaction force of the linear direction. In addition, since it is an electromagnetic drive type motor, AC magnetic field leakage from the coils and DC magnetic field leakage from the magnets are generated from the motors 33, 45 for arm rotation.

Further, the material point shifts due to the aforementioned type of arm extension operation, and vibration is produced.

For cancellation mechanisms, the motor unit 10 is equipped with two stages of upper and lower reaction force cancellation motors 59, 63 that are arranged outside the aforementioned outer core 31 and two stages of upper and lower counterweight sleeves (CW sleeves) 51, 53.

The upper cancellation motor 59 includes at least a coil (cancellation rotor) 59a and a magnet (cancellation stator) 59b. The coil 59a is secured along the inner surface of the upper CW sleeve 51. The magnet 59b is provided or secured along the outer surface of the upper portion of the outer core 31 so to oppose the coil 59a. The cancellation motor 59 may be arranged at a position approximately the same height as the first arm drive shaft rotation motor 33 and the second arm drive shaft rotation motor 45.

The lower cancellation motor (RC motor) 63 includes at least a coil (RC mover) 63a and a magnet (RC stator) 63b. The coil 63a is provided or secured along the inner surface of the lower CW sleeve 53. The magnet 63b is provided or secured along the outer surface of the lower portion of the outer core 31 to oppose the coil 63a. This RC motor 63 may be arranged at a position approximately the same height as the linear motor 47 for movement in the Z direction.

The CW sleeves 51, 53 may be arranged between the side wall 13 and the casing 11 and the outer core 31 to be concentric with the center axis P1 of the motor unit. For example, the aforementioned CW sleeve 51 is such that the upper portion of the outer surface is supported by the side wall 13 of the main unit portion of the casing via a bearing 55, and the lower portion of the inner surface is supported by the center of the outer surface of the outer core 31 via a bearing 57. In addition, as described above, the coil 59a of the upper cancellation motor 59 is provided or secured along the inner surface of the upper CW sleeve 51, and the upper CW sleeve 51 is driven by the upper cancellation motor 59 and rotates centering on axis P1.

For example, the aforementioned lower CW sleeve 53 is such that the lower portion of the inner surface is supported by the outer surface of the outer core 31 via a bearing 61. A certain amount of gap is opened between the lower end of the lower CW sleeve 53 and the bottom wall 15c of the casing. In addition, as described above, coil 63a of cancellation motor 63 is provided or secured along the inner surface of the lower CW sleeve 53, and the lower CW sleeve 53 is driven by that motor 63 and moved up and/or down in the Z direction along axis P1.

According to an embodiment of the invention, the magnet (cancellation stator) 59b of the cancellation magnet 59 is secured to the outer circumference of the outer core 31. Further, the outer core 31 is provided or secured to the ceiling member 19 of the casing along with the inner core 29 to which the main stators 33b, 45b for rotation of their respective arm drive shafts 23, 21 are provided or secured. Therefore, the cores 29, 31 may be considered a unit. For example, the reaction force applied to the stators 33b, 45b when their respective motors 33, 45 for the rotation of both shafts are rotated is transmitted to the cancellation rotor 59b of the cancellation motor 59 via the inner core 29 and the outer core 31. Therefore, by rotating the cancellation rotor 59a and the upper CW sleeve 51 in directions opposite those of the shafts 21, 23, a reaction force that cancels the aforementioned reaction force is applied to the cancellation stator 59b. When this occurs, the reaction forces (torque) of the motors 33, 45, 59 are cancelled within the cores 29, 31, and the reaction forces do not occur outside the motor unit 10. As such, the motor unit 10 does not vibrate (applies vibration to) to the apparatus (exposure apparatus) that is attached to it.

Reaction force cancellation in the arm extension direction (linear direction), is discussed hereinbelow.

Figure 6:
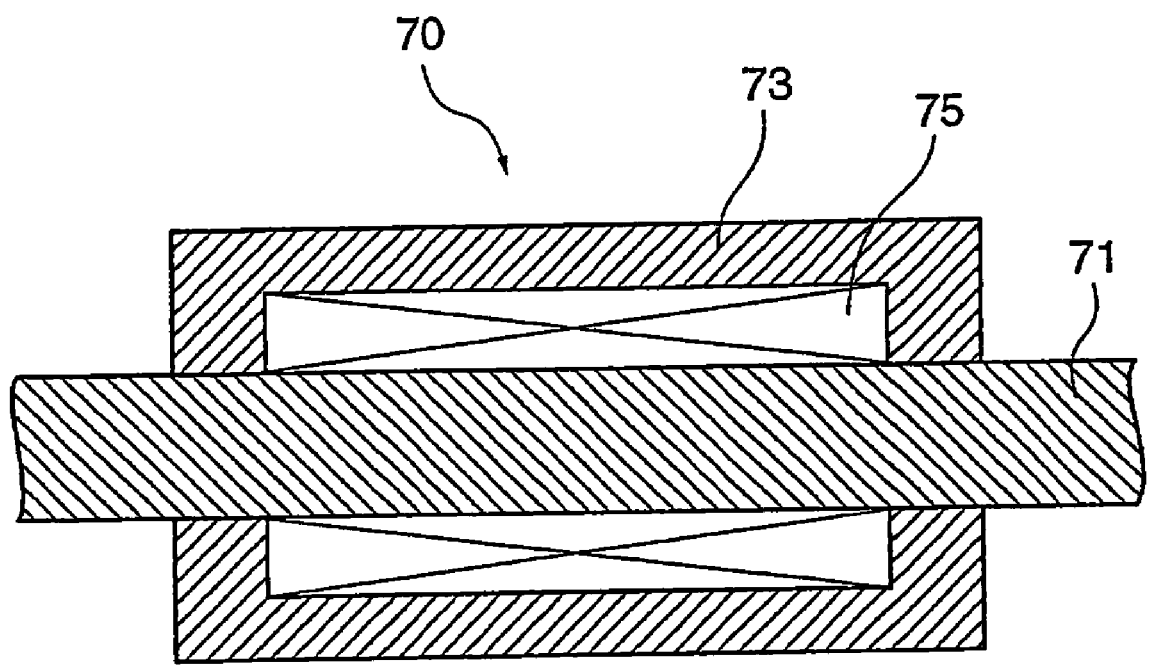
FIG. 6 is a cross-sectional view that schematically shows the structure of a mass balancer of the substrate loader of FIG. 2.

As shown in FIG. 2 and FIG. 6, a mass balancer 70 that extends in a direction (diameter direction) opposite that of the arm is provided at an end portion (the left side of the figure) of first arm 50.

For example, the mass balancer 70 is configured with or may be a unit that includes a guide 71 that extends in a direction opposite that of the first arm 50 and a counterweight (CW) 73 able to slide along that guide 71. The weight of the counterweight 73 corresponds with the weight of portions in front of the second joint 101 (second arm 100, third arm 120, end effector 125, motor 110, etc.). An actuator 75 is provided between the guide 71 and the counterweight 73. A non-magnetic ultrasonic linear motor, or the like, may be used as the actuator 75. The counterweight 73 is further able to slide in both directions on the guide 71 via this actuator 75.

This mass balancer 70 operates to cancel the acceleration and/or deceleration of the mass that occurs in conjunction with the extension and/or retraction of at least one of the first through third arms. Specifically, acceleration and deceleration in the direction opposite the acceleration and/or deceleration applied to the equivalent mass of the arm is applied to the counterweight 73, the reaction force is balanced within the arm, and the reaction force does not go outside the motor unit 10.

As shown in at least FIG. 3, there is provided at the outer surface of the casing 11 a magnetic shield 140 that covers the outer surface of the casing 11 while leaving a certain gap (e.g., several mm). For example, the magnetic shield 140 includes a main unit portion 141 that encloses the main unit portion 17 of the casing 11 and the lid portion 143 that covers the ceiling portion 19. The magnetic shield 140 may be made of a high induction rate material, such as Permalloy.

The magnetic shield 140 operates to cancel at least the DC magnetic field leakage emitted from the magnets 33b, 45b, 47b, 59b, 63b of the motors within the motor unit 10.

The operation of the mechanism that cancels the magnetism and the reaction force of the motor accompanying the operation of substrate loader 1 is described hereinbelow.

According to an embodiment of the invention, the substrate loader 1 transfers the wafer or the substrate generally between the cassette and the stage. The substrate loader 1 may adopt a rotating operation that takes the substrate from on top of the end effector 125 and places it on top of the target position, an unrotating operation that removes the substrate from on top of the target position and puts it on top of the end effector 125, and a standby operation. The initial position of the substrate loader 1 is a status in which the arms 80, 100, 120 are substantially linearly aligned.

Figure 7:
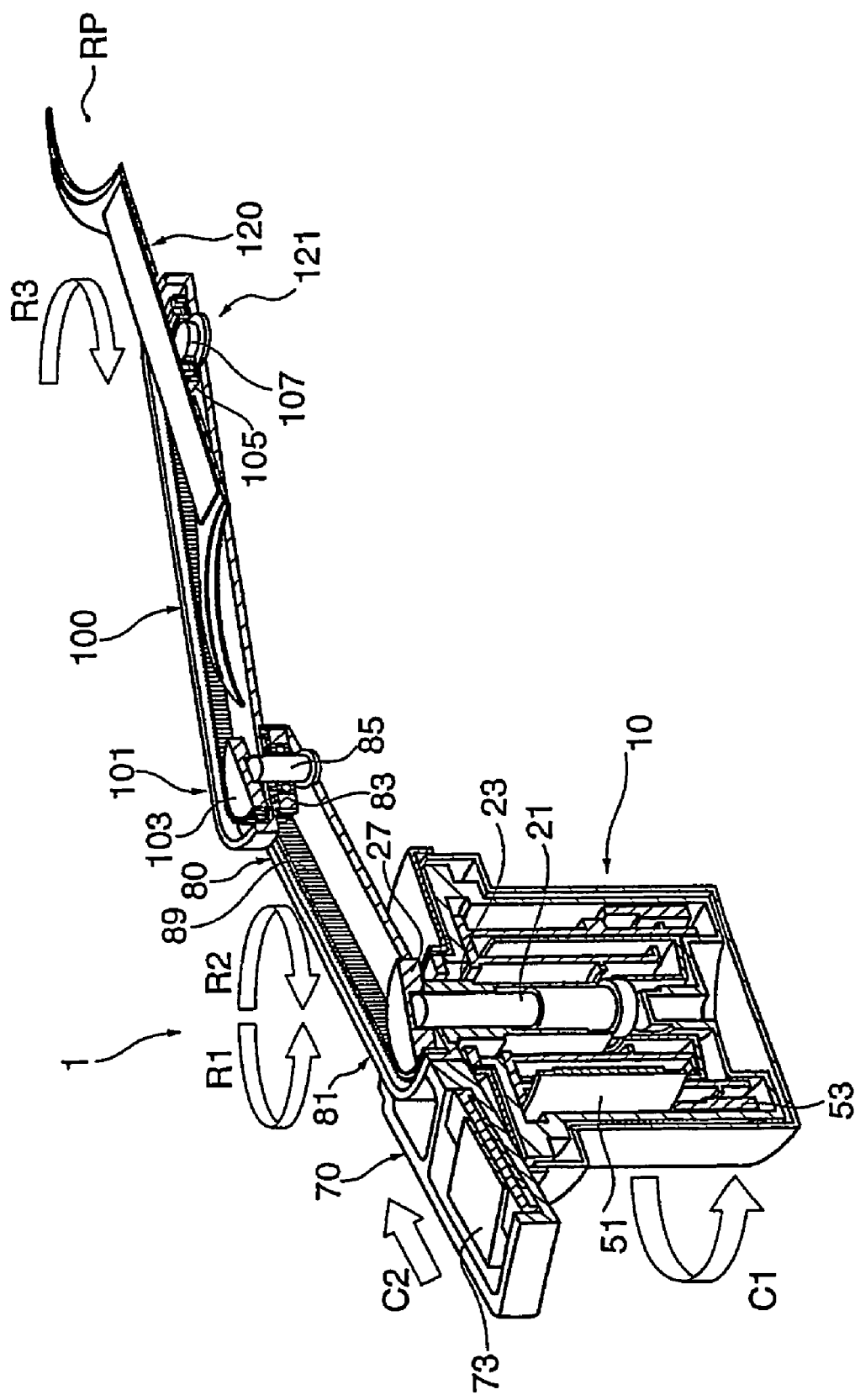
FIG. 7 is a cross-sectional oblique view that shows an operation status of the substrate loader of FIG. 1.
Figure 8:
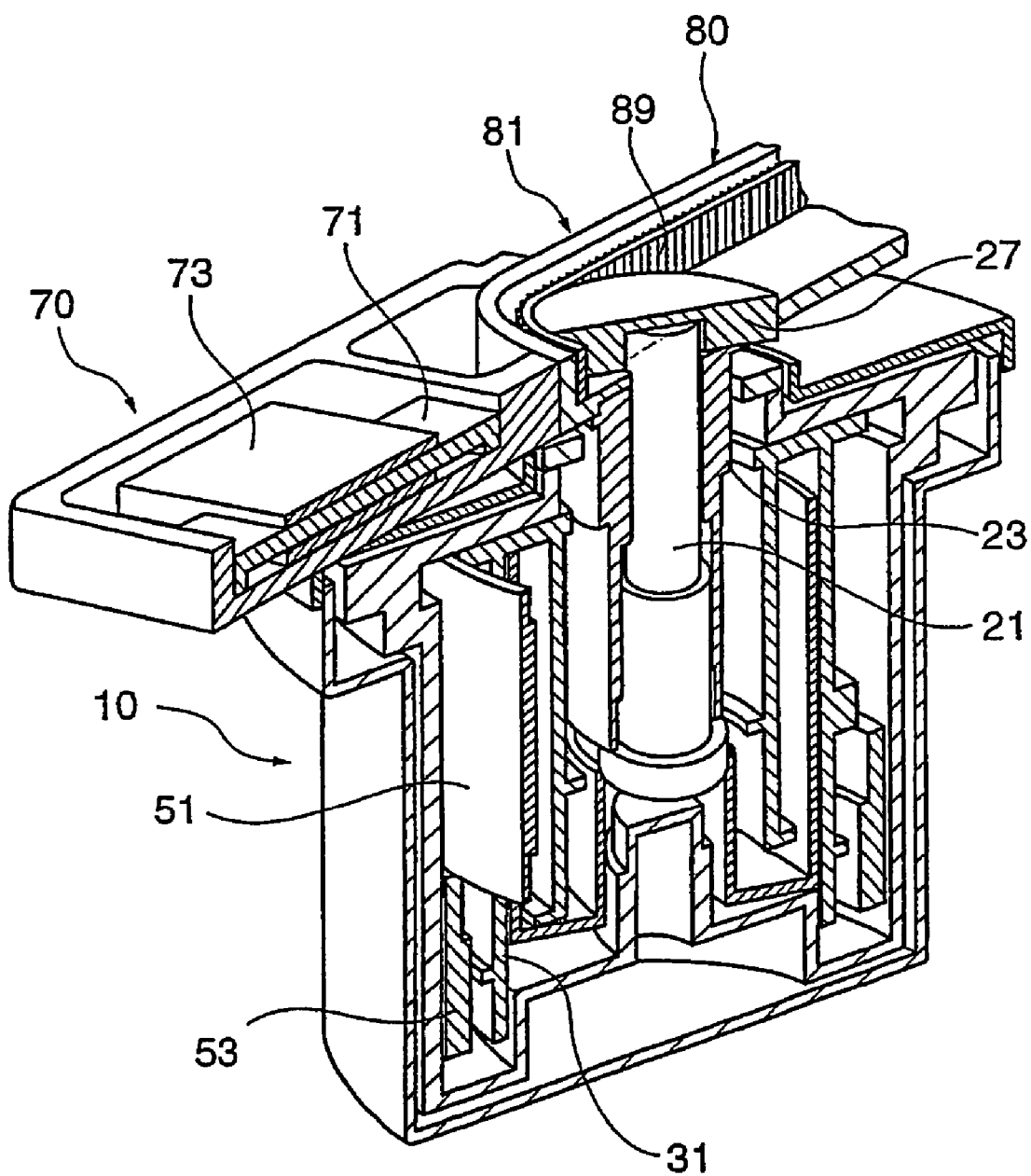
FIG. 8 is a cross-sectional oblique view that shows an enlargement of the substrate loader of FIG. 7.

FIG. 7 is a cross-sectional oblique view of the operating status of the substrate loader in FIG. 1. FIG. 8 is a cross-sectional oblique view that shows an enlargement of the substrate loader in FIG. 7. In FIGS. 7 and 8, the rotation directions discussed below refer to a status as seen from the top to the bottom.

This status of FIGS. 7 and 8 is a status in which the first arm 80 rotates in a somewhat counterclockwise direction centering on the first joint 81, the second arm 100 rotates in a somewhat clockwise direction centering on the second joint 101, and the third arm 120 rotates in a somewhat counterclockwise direction centering on the third joint 121. The center of the end effector 125 of the third arm 120 is positioned at rotating point RP.

For example, in the motor unit 10, the first arm drive shaft rotation motor 33 rotates counterclockwise (arrow R1), and the second arm drive shaft rotation motor 45 rotates clockwise (arrow R2).

As such, both drive shafts 23, 21 rotate in opposite directions, and a rotation reaction force equivalent to approximately the difference in the rotational torque of both shafts is applied to the inner core 29 to which the main stators 33b, 45b of the rotation motors 33, 45 of their respective shafts are secured. Clockwise reaction force torque is applied to the inner core 29. Therefore, by rotating the cancellation rotor 59a and the CW sleeve 51 counterclockwise, which is a direction opposite the direction of the rotational torque of both shafts, a reaction force that cancels the aforementioned reaction force is applied to the cancellation stator 59b. Through this, the reaction forces (torque) of the motors 33, 45, 59 are mutually cancelled within the cores 29, 31, and they do not go outside of the motor unit 10.

Moreover, the actuator 75 of the mass balancer 70 is driven to move the counterweight 73 in a direction that faces the first arm 80 (diameter direction, arrow C2) along a guide 71. Accordingly, the acceleration and deceleration of mass that occurs in conjunction with the extension and retraction of the first through third arms is cancelled. For example, the acceleration or deceleration applied to the equivalent mass of the arms is applied to the counterweight 73, the reaction force within the arm is balanced, and the reaction force does not occur outside the motor unit 10.

Figure 9:
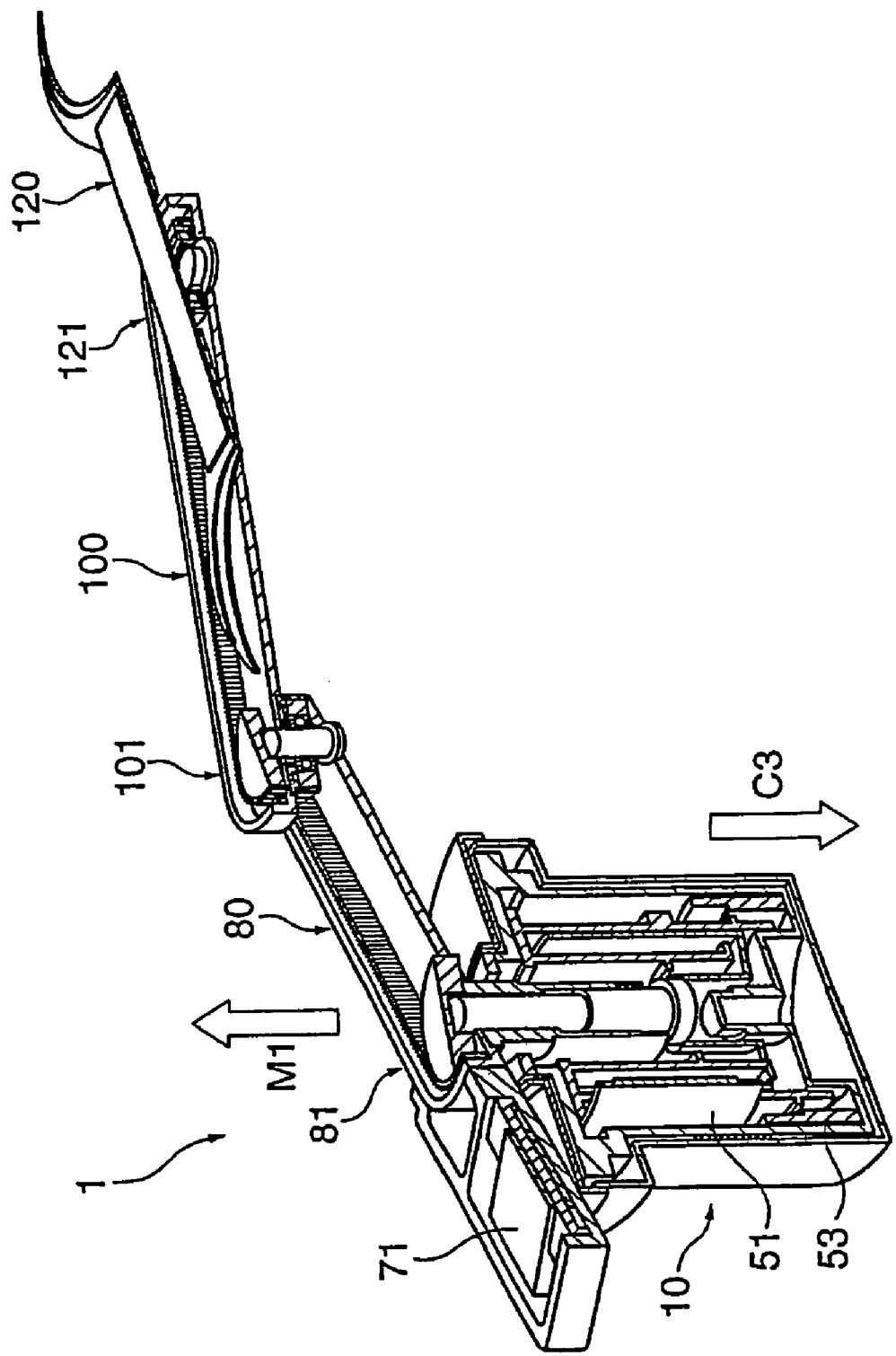
FIG. 9 is a cross-sectional oblique view that shows a raising and lowering operation status of the substrate loader of FIG. 1.
Figure 10:
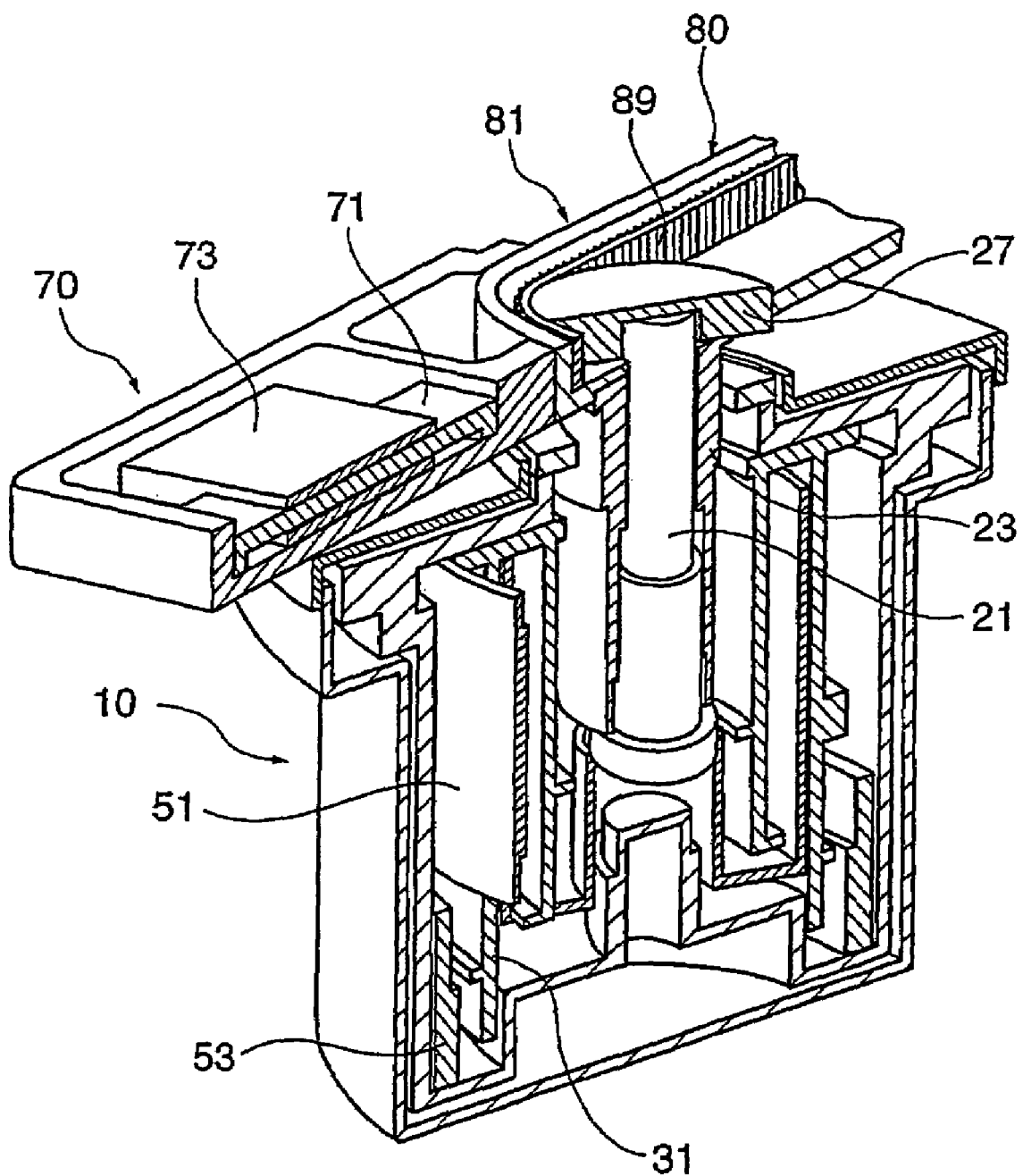
FIG. 10 is a cross-sectional oblique view that shows an enlargement of the substrate loader of FIG. 9.

FIG. 9 is a cross-sectional oblique view that shows a status of the raising and lowering operation of the substrate loader of FIG. 1. FIG. 10 is a cross-sectional oblique view that shows an enlargement of the substrate loader of FIG. 9.

The status in FIGS. 9 and 10 shows the status when the entire arm has been raised in the Z direction from the status in FIG. 7. For example, the linear motor 47 is driven upward (arrow M1), and the first arm drive shaft 23 and the second arm drive shaft 21 are both driven to be raised in the Z direction.

According to the foregoing, the RC motor is driven downward (arrow C3), and the lower CW sleeve 53 is moved downward. Through this, the acceleration and/or deceleration of mass that occurs in conjunction with the movement of at least one of the first through third arms upward is cancelled. In other words, the acceleration or deceleration applied to the equivalent mass of the arms is applied to the lower CW sleeve 53, the reaction force within the motor unit 10 is balanced, and the reaction force does not go outside the motor unit 10.

Figure 11:
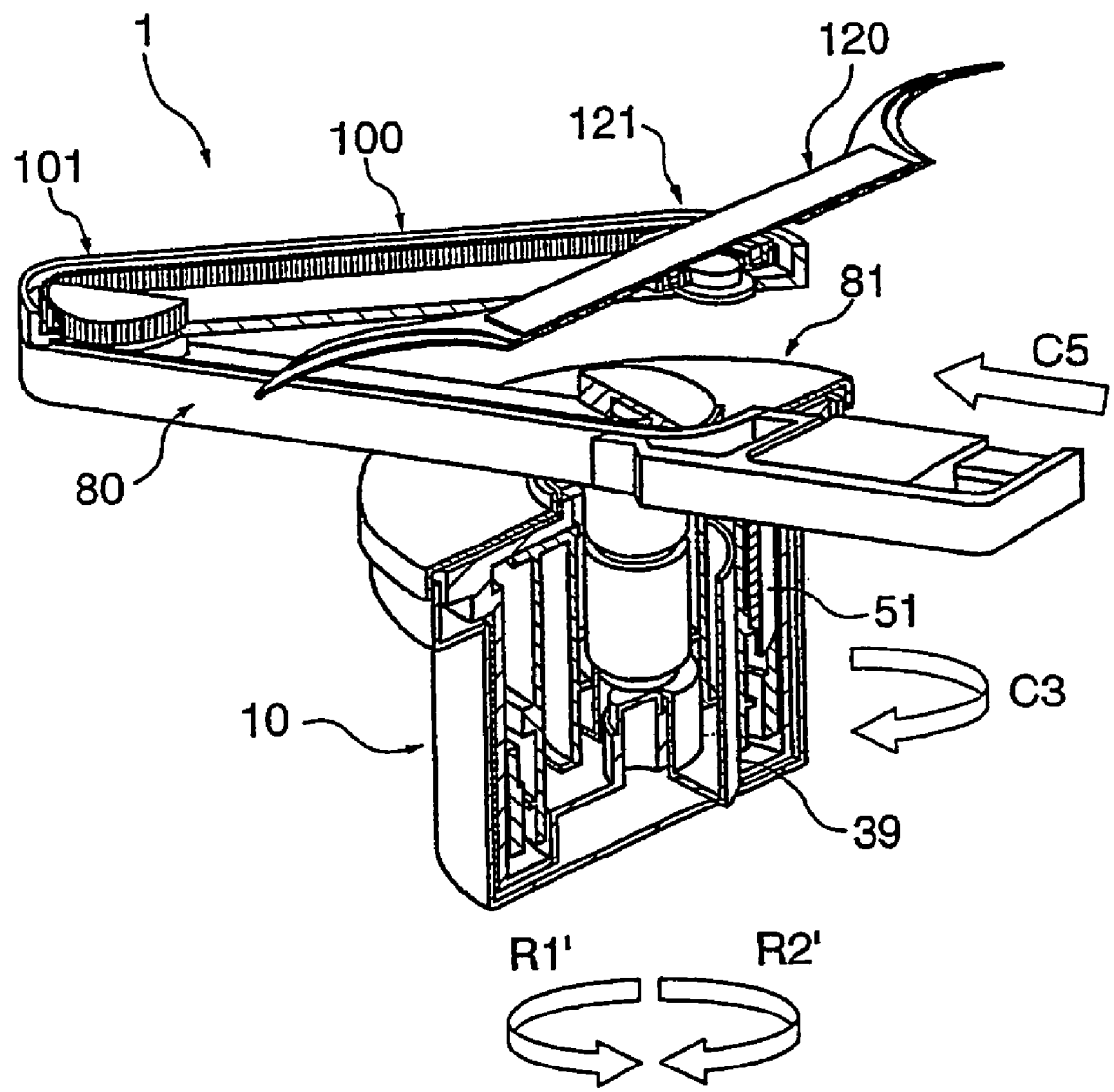
FIG. 11 is a cross-sectional oblique view that shows a status during standby of the substrate loader of FIG. 1.
Figure 12:
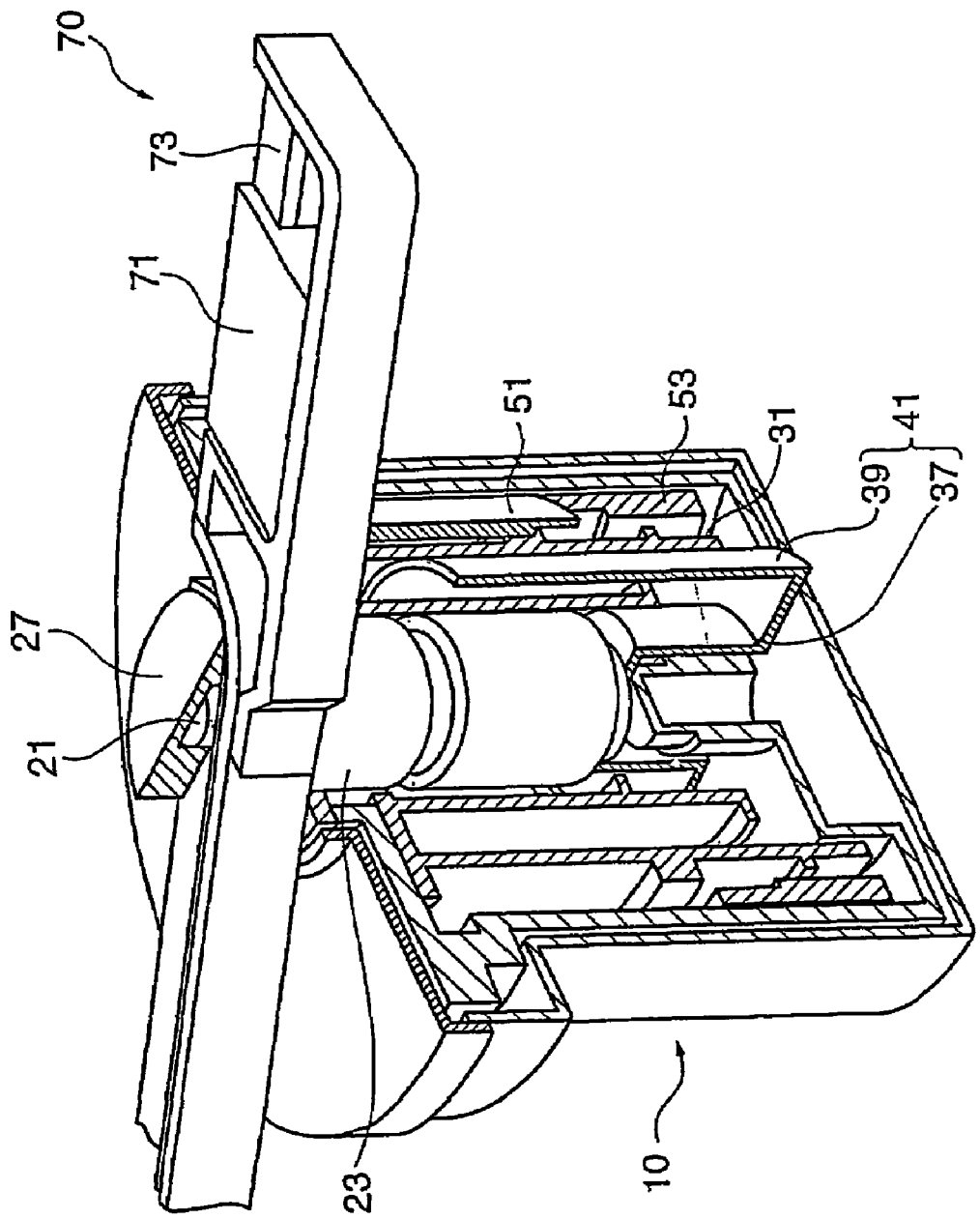
FIG. 12 is a cross-sectional oblique view that shows an enlargement of the substrate loader of FIG. 11.

FIG. 11 is a cross-sectional oblique view that shows a standby status of the substrate loader of FIG. 1. FIG. 12 is a cross-sectional oblique view that shows an enlargement of the substrate loader of FIG. 1.

FIGS. 11 and 12 illustrate the standby status when the second arm 100 is retracted approximately 90°. For example, when the first arm 80 is rotated from the initial status approximately 90° counterclockwise centering on the first joint 81, the second arm 100 is rotated from the initial status approximately 90° clockwise centering on the second joint 101 (180° rotation with respect to the first arm 80), and both arms 80, 100 are folded to be stacked. In addition, the third arm 120 is angularly positioned at the initial position.

Further, in the motor unit 10, when the first arm drive shaft rotation motor 33 is rotated counterclockwise (arrow R1'), the second arm drive shaft rotation motor 45 is rotated clockwise (arrow R2').

To cancel the rotation reaction force applied to the stators that are secured to their respective shafts, the cancellation motor is driven to rotate the upper CW sleeve 51 clockwise (arrow C3). Here, while the arm rotation directions are the same as in FIG. 7, the rotation direction of the CW sleeve 51 differs because the generated torque resulting from the revolving of the arm around the shaft is cancelled.

Further, the actuator 75 of the mass balancer 70 may be driven to move the weight 71 in a direction that approaches the first arm 80 (arrow C5).

Figure 13:
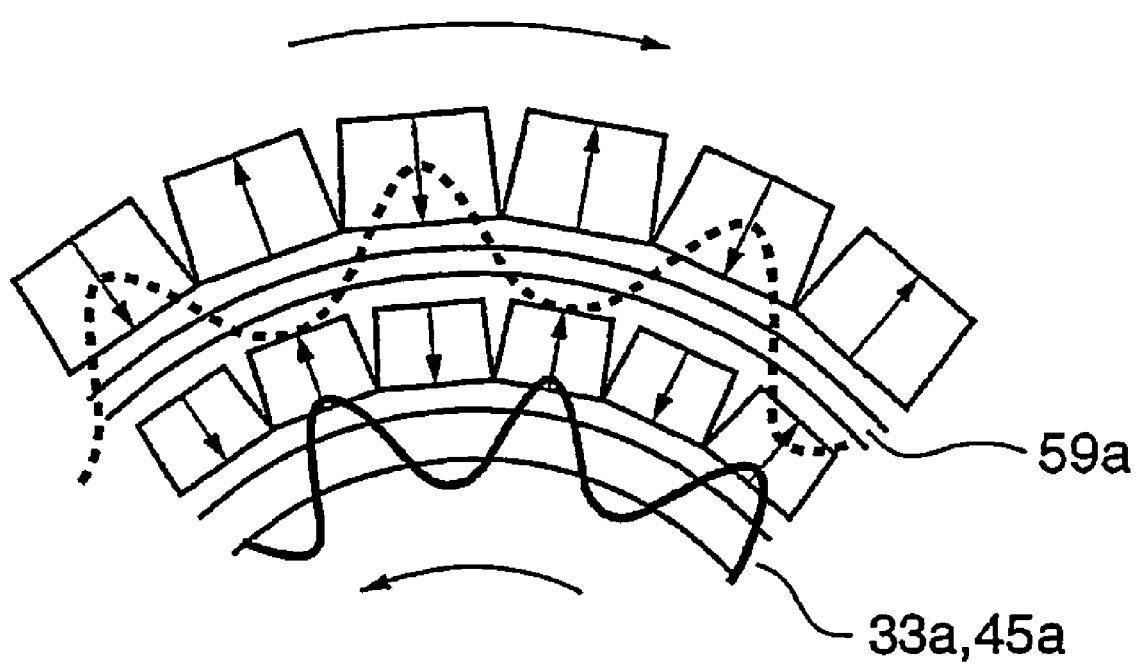
FIG. 13 is a drawing that schematically shows a status of the magnetic field accompanying operation of the reaction force cancellation mechanism.
Figure 14:
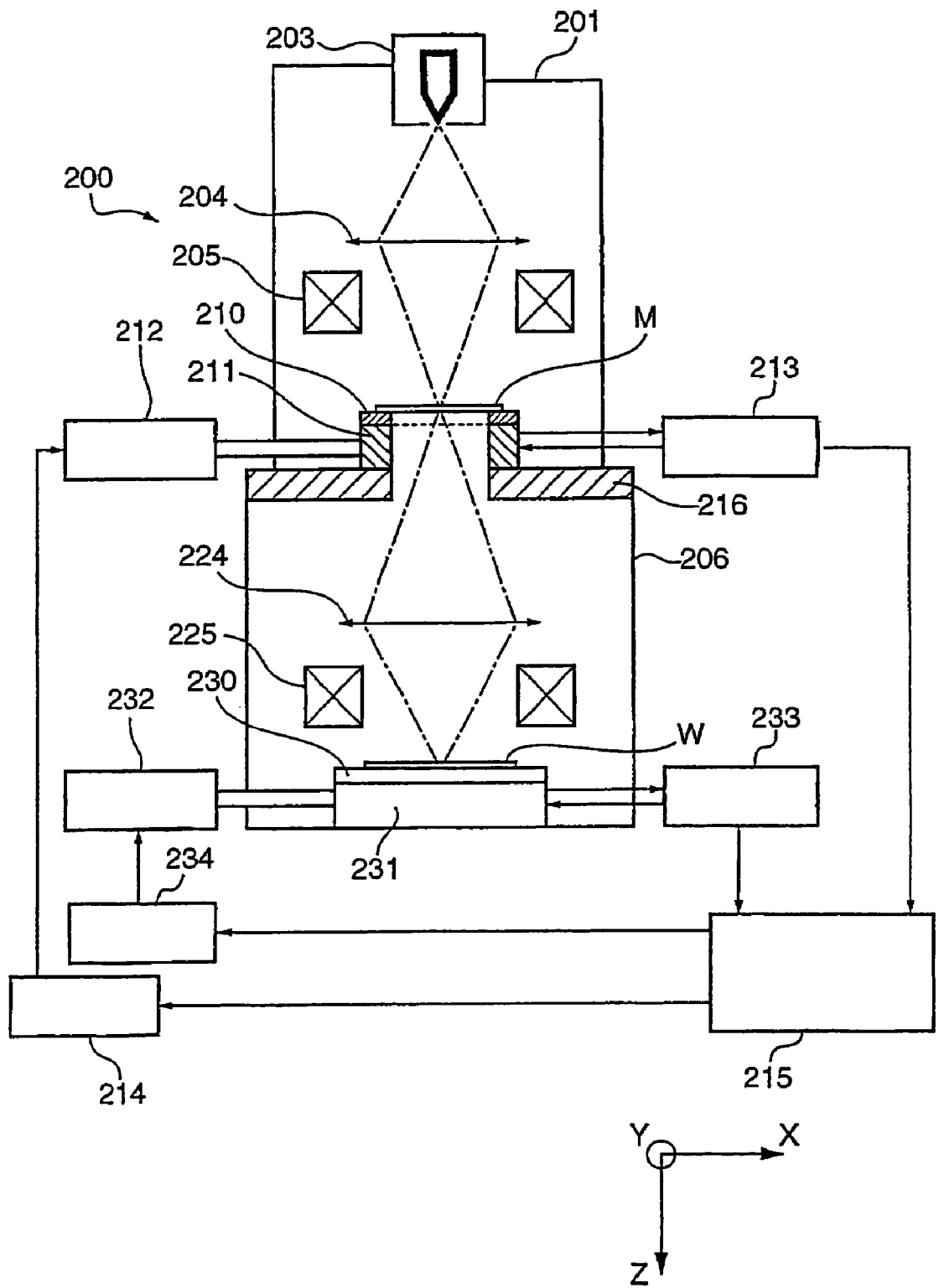
FIG. 14 is a drawing that shows an image formation-related and control system overview of the entire optical system of an electron beam exposure apparatus of a conventional projection exposure system.

FIG. 13 is a drawing that shows the status of the magnetic field accompanying an operation of the reaction force cancellation mechanism. In FIG. 13, the dashed line indicates the magnetic field generated from the cancellation rotor 59a of the cancellation motor 59, and the solid line shows the magnetic field that synthesizes the magnetic fields generated by the main rotor 33a, 45a of motor 33 and 45. In addition, the upper side arrow indicates the rotation direction of the cancellation motor 59, and the lower side arrow indicates the rotation direction of the energy that synthesizes the rotation energy of the motor 33 and 45.

Therefore, as shown in FIG. 13, the rotation direction of the cancellation motor 59 and the rotation direction of the energy that synthesizes energy of the rotation of motor 33 and 45 for rotation of the arms are opposite directions, and the phases of the magnetic fields of the phases of both motors are controlled such that the phases are shifted by approximately 180°.

According to the foregoing operation, the magnetic fields of the motors are offset overall and the leaked AC magnetic field is cancelled.

Figure 15:
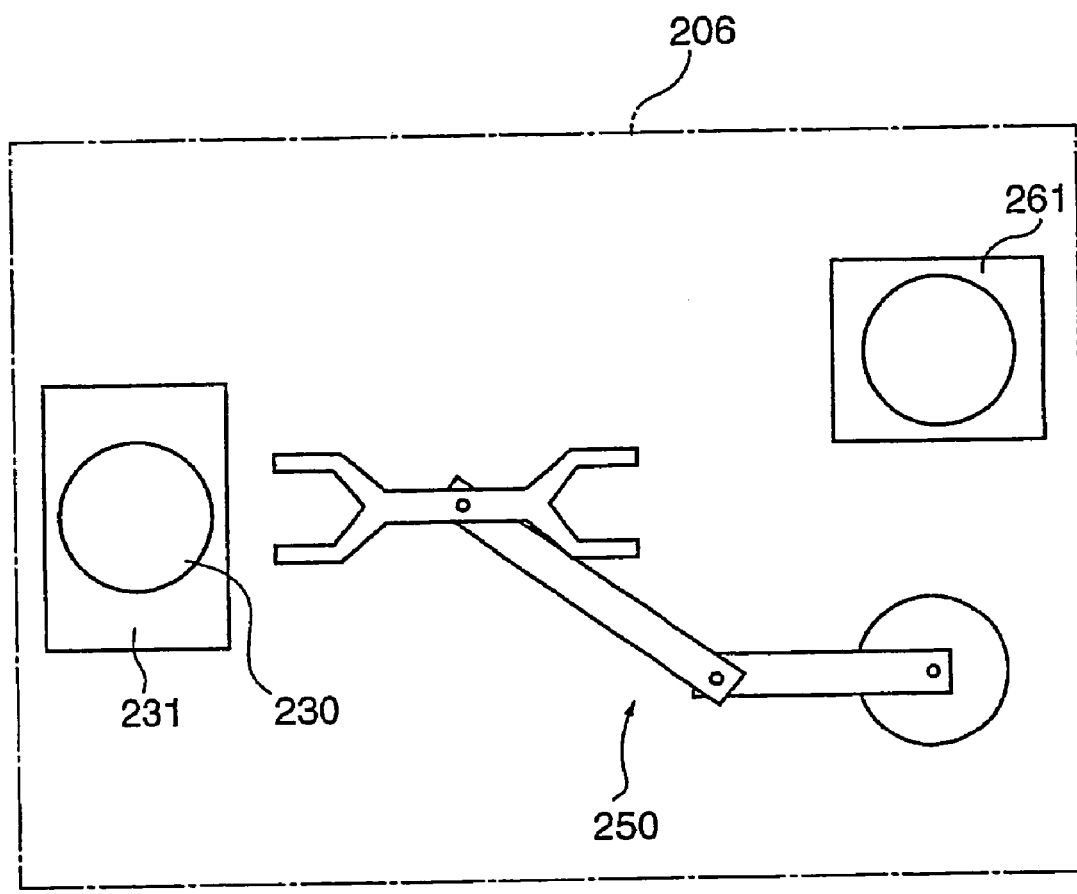
FIG. 15 is a plan view that schematically describes the wafer conveyance mechanism within a common wafer chamber according to a conventional mechanism.

In addition, during the aforementioned operation shown in FIG. 15, the DC magnetic field leakage from the magnets of the motors is shielded by magnetic shield 140.

For example, the substrate loader 1 is provided or installed in the wafer chamber 206 (see FIG. 15) of the exposure apparatus. The substrate loader 1 performs a wafer transfer or conveyance. During the wafer conveyance, the exposure operation is simultaneously performed. Thus, the generation of magnetic field leakage and/or vibration is reduced in the aforementioned way. Further the forgoing operation does not affect the path of the electron beam.

Therefore, according to at least the foregoing discussion and embodiments, a motor is provided that restricts magnetic field leakage and generation of vibration. In addition, an exposure apparatus is provided that performs the substrate conveyance operation and exposure operation simultaneously and that increases throughput by using a substrate loader that includes a robot equipped with such a motor and which is capable of handling the end effector at high speed.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A motor comprising:
   a drive shaft;
   a casing that covers the motor;
   a main rotor attached with the drive shaft;
   a main stator that is attached to the casing, opposes the main rotor and causes an electromagnetic force to act between the main rotor and the main stator to drive the drive shaft;
   a stator for reaction force cancellation, attached with the main stator as an unit and moves relative to the main rotor together with the main stator;
   a rotor for reaction force cancellation, opposing the stator for reaction force cancellation; and
   a counterweight sleeve attached with the rotor for reaction force cancellation,
   wherein a reaction force is applied to the main stator via the drive shaft when the counterweight sleeve rotates in a direction opposite to that of the drive shaft, and
   wherein the reaction force is cancelled.

2. The motor of claim 1, wherein the reaction force applied to the main stator is attributable to moments of inertia of the drive shaft and the main rotor.

3. The motor of claim 1, further comprising:
   a stator for magnetic cancellation, attached with the main stator; and
   a rotor for magnetic cancellation, opposing the stator for magnetic cancellation,
   wherein magnetism is generated by the main rotor and the main stator via the drive shaft when magnetism is generated by the stator for magnetic cancellation and the rotor for magnetic cancellation, and
   wherein magnetism is cancelled.

4. The motor of claim 3, further comprising
   a magnetic shield made with a material having a high magnetic induction ratio that covers a first area of the motor and does not cover a second area of the motor.

5. A substrate loader having at least one arm and the electromagnetic rotation type motor of claim 3, comprising:
   an extension mechanism provided with the at least one arm; and
   a raising and lowering mechanism provided with the at least one arm,
   wherein the electromagnetic rotation type motor is a drive source of the extension mechanism and the raising and lowering mechanism.

6. The motor of claim 1, wherein
   the stator for reaction force cancellation additionally performs magnetic cancellation;
   the rotor for reaction force cancellation, opposing the stator for reaction force cancellation, additionally performs magnetic cancellation, and
   wherein magnetism is generated by the main rotor and the main stator via the drive shaft when magnetism is generated by the stator for reaction force cancellation and the rotor for reaction force cancellation, and
   wherein magnetism is cancelled.

7. The motor of claim 6, further comprising
   a magnetic shield made with a material having a high magnetic induction ratio that covers a first area of the motor and does not cover a second area of the motor.

8. A substrate loader having at least one arm and the electromagnetic rotation type motor of claim 6, comprising:
   an extension mechanism provided with the at least one arm; and
   a raising and lowering mechanism provided with the at least one arm,
   wherein the electromagnetic rotation type motor is a drive source of the extension mechanism and the raising and lowering mechanism.

9. A substrate loader having at least one arm and the electromagnetic rotation type motor of claim 1, comprising:
   an extension mechanism provided with the at least one arm; and
   a raising and lowering mechanism provided with the at least one arm,
   wherein the electromagnetic rotation type motor is a drive source of the extension mechanism and the raising and lowering mechanism.

10. The substrate loader of claim 9, further comprising:
    a main mover attached with the at least one arm and provided with the raising and lowering mechanism; and a mover for reaction force cancellation that opposes the stator, wherein the counterweight sleeve is attached with the mover, wherein the reaction force is applied to the main stator via the raising and/or lowering of the at least one arm by moving the counterweight sleeve in a direction opposite to the at least one arm, and wherein the reaction force is cancelled.

11. An exposure apparatus having the substrate loader of claim 9, comprising:

a substrate conveyance system to convey at least one substrate; and an optical system that selectively irradiates an energy beam onto the at least one substrate to form a pattern on the at least one substrate.

12. A robot having at least one arm and an electromagnetic rotation type motor that is a drive source for the at least one arm, comprising:

a drive shaft;

a casing that covers the motor;

a main rotor attached with the drive shaft;

a main stator that is attached to the casing, opposing the main rotor, and causing an electromagnetic force to act between the main rotor and the main stator to drive the drive shaft;

a stator for reaction force cancellation, attached with the main stator as an unit and moves relative to the main rotor together with the main stator;

a rotor for reaction force cancellation, opposing the stator for reaction force cancellation; and a counterweight sleeve attached with the rotor for reaction force cancellation, wherein the reaction force is applied to the main stator via the drive shaft by rotating the counterweight sleeve in a direction opposite that of the drive shaft, and wherein the reaction force is cancelled.

13. The robot of claim 12, wherein the reaction force applied to the main stator is attributable to moments of inertia of the drive shaft and the main rotor.

14. The robot of claim 12, further comprising:

a stator for magnetic cancellation, attached with the main stator; and a rotor for magnetic cancellation, opposing the stator for magnetic cancellation, wherein magnetism is generated by the main rotor and the main stator via the drive shaft when magnetism is generated by the stator for magnetic cancellation and the rotor for magnetic cancellation, is cancelled.

15. The robot of claim 14, further comprising:

a magnetic shield made of a material having a high magnetic induction ratio that covers a first area of the electromagnetic rotation motor and does not cover a second area of the electromagnetic rotation motor.

16. The robot of claim 12, wherein the stator for reaction force cancellation additionally performs magnetic cancellation, the rotor for reaction force cancellation additionally performs magnetic cancellation, and wherein magnetism is generated by the main rotor and the main stator via the drive shaft when magnetism is generated by the stator for reaction force cancellation and the rotor for reaction force cancellation, and wherein magnetism is cancelled.

17. The robot according to claim 16, further comprising:

a first arm driven via a first arm drive shaft of the electromagnetic rotation type motor; and a second arm driven via a drive belt via a second arm drive shaft of the electromagnetic rotation type motor, wherein the reaction forces of the main stator for the first arm drive shaft and a main stator for the second arm drive shaft are cancelled.

18. The robot of claim 17, further comprising a raising and lowering mechanism that raises and/or lowers the first arm, wherein the raising and lowering mechanism comprises:

a main mover attached with the first arm;

the main stator opposing the main mover;

the stator for reaction force cancellation, attached with the main stator; and a mover, for reaction force cancellation, opposing the stator, wherein the counterweight sleeve is attached with the mover, wherein a reaction force is applied to the main stator via the raising and/or lowering of the first arm when the counterweight moves in a direction opposite to the first arm, and wherein the reaction force is cancelled.

19. The robot of claim 16, further comprising:

a magnetic shield made of a material having a high magnetic induction ratio that covers a first area of the electromagnetic rotation motor and does not cover a second area of the electromagnetic rotation motor.

20. The robot of claim 12, further comprising:

a first arm driven via a first arm drive shaft of the electromagnetic rotation type motor; and a second arm driven via a drive belt via a second arm drive shaft of the electromagnetic rotation type motor, wherein the reaction forces of the main stator for the first arm drive shaft and a main stator for the second arm drive shaft are cancelled.

21. The robot of claim 20, further comprising a raising and lowering mechanism that raises and/or lowers the first arm, wherein the raising and lowering mechanism comprises:

a main mover attached with the first arm;

the main stator opposing the main mover;

the stator for reaction force cancellation that is attached with the main stator; and a mover for reaction force cancellation, opposing the stator, wherein the counterweight is attached with the mover, and wherein a reaction force is applied to the main stator via the raising and/or lowering of the first arm when the counterweight sleeve moves in a direction opposite to the first arm, and wherein the reaction force is cancelled.

22. The robot of claim 12, further comprising:

a magnetic shield made of a material having a high magnetic induction ratio that covers a first area of the electromagnetic rotation motor and does not cover a second area of the electromagnetic rotation motor.

* * * * *

UNITED STATES PATENT AND TRADEMARK OFFICE
CERTIFICATE OF CORRECTION

PATENT NO. : 7,336,012 B2
APPLICATION NO. : 11/030155
DATED : February 26, 2008
INVENTOR(S) : Keiichi Tanaka Page 1 of 1

It is certified that error appears in the above-identified patent and that said Letters Patent is hereby corrected as shown below:

Column 20, Line 49, after "mover," delete "and".

Signed and Sealed this

Second Day of September, 2008

JON W. DUDAS
*Director of the United States Patent and Trademark Office*